United States Patent
Wijesundara et al.

(10) Patent No.: US 10,064,744 B2
(45) Date of Patent: Sep. 4, 2018

(54) FLUID-DRIVEN BUBBLE ACTUATOR ARRAYS

(71) Applicant: THE BOARD OF REGENTS OF THE UNIVERSITY OF TEXAS SYSTEM, Austin, TX (US)

(72) Inventors: Muthu Wijesundara, Arlington, TX (US); Wei Carrigan, Arlington, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 5 days.

(21) Appl. No.: 15/107,969

(22) PCT Filed: Dec. 24, 2014

(86) PCT No.: PCT/US2014/072338
§ 371 (c)(1),
(2) Date: Jun. 24, 2016

(87) PCT Pub. No.: WO2015/100408
PCT Pub. Date: Jul. 2, 2015

(65) Prior Publication Data
US 2016/0331556 A1    Nov. 17, 2016

Related U.S. Application Data

(60) Provisional application No. 61/941,262, filed on Feb. 18, 2014, provisional application No. 61/920,903, filed on Dec. 26, 2013.

(51) Int. Cl.
*A61F 2/54* (2006.01)
*A61G 7/057* (2006.01)
(Continued)

(52) U.S. Cl.
CPC ............. *A61F 2/54* (2013.01); *A42B 3/122* (2013.01); *A61F 2/68* (2013.01); *A61F 2/78* (2013.01);
(Continued)

(58) Field of Classification Search
CPC ........ B25J 15/0023; A42B 3/122; B32B 7/08; B32B 3/266; B32B 3/28; B32B 2535/00;
(Continued)

(56) References Cited

U.S. PATENT DOCUMENTS 3,283,799 A    11/1966 Barbera
3,538,628 A    11/1970 Einstein
(Continued)

OTHER PUBLICATIONS

Board et al. "A comparison of trans-tibial amputee suction and vacuum socket conditions." Prosthetics and Orthotics International. vol. 25, No. 3, 2001, pp. 202-209.
(Continued)

*Primary Examiner* — Stephen A Vu
(74) *Attorney, Agent, or Firm* — Norton Rose Fulbright US LLP

(57) ABSTRACT

This disclosure includes bubble actuator arrays and methods for making and using the same. Some bubble actuator arrays include a first flexible layer having a substantially flat first portion and a plurality of second portions that protrude away from the first portion to define chambers, a flexible second layer sealed to the first layer to define a plurality of cells in the chambers and between the layers, and where the array can be coupled to a fluid source such that the internal pressures of the cells can be varied. Some of the present methods include adjusting with a processor and fluid source the pressure in the cells of an array. Others of the present methods include placing sacrificial material into chambers of a molded first layer such that a plurality of cells is formed
(Continued)

when a second layer is molded coincident to the first and the sacrificial material is removed.

19 Claims, 13 Drawing Sheets

(51) Int. Cl.
| | |
|---|---|
| B25J 15/00 | (2006.01) |
| A42B 3/12 | (2006.01) |
| A61F 2/68 | (2006.01) |
| A61F 2/78 | (2006.01) |
| B32B 3/26 | (2006.01) |
| B32B 3/28 | (2006.01) |
| B32B 7/08 | (2006.01) |
| B32B 27/08 | (2006.01) |
| F15B 15/10 | (2006.01) |
| A61F 2/50 | (2006.01) |
| A61F 2/74 | (2006.01) |

(52) U.S. Cl.
CPC ...... *A61G 7/05776* (2013.01); *B25J 15/0023* (2013.01); *B32B 3/266* (2013.01); *B32B 3/28* (2013.01); *B32B 7/08* (2013.01); *B32B 27/08* (2013.01); *F15B 15/10* (2013.01); *A61F 2002/5012* (2013.01); *A61F 2002/745* (2013.01); *B32B 2307/51* (2013.01); *B32B 2307/546* (2013.01); *B32B 2307/732* (2013.01); *B32B 2535/00* (2013.01)

(58) Field of Classification Search
CPC .............. B32B 2307/546; B32B 27/08; B32B 2307/732; B32B 2307/51; A61F 2/68; A61F 2/78; A61F 2/54; A61F 2002/745; A61G 7/05776; F15B 15/10
See application file for complete search history.

(56) References Cited

U.S. PATENT DOCUMENTS

| | | | |
|---|---|---|---|
| 3,574,386 A | 4/1971 | Frost | 294/87.1 |
| 3,834,046 A | 9/1974 | Fowler | 36/28 |
| 5,156,629 A | 10/1992 | Shane et al. | 623/37 |
| 5,237,501 A | 8/1993 | Gusakov | 600/587 |
| 5,267,365 A | 12/1993 | Walter | 5/683 |
| 5,916,664 A | 6/1999 | Rudy | 428/178 |
| 6,092,249 A | 7/2000 | Kamen et al. | 5/653 |
| 8,127,373 B1 | 3/2012 | Fodemski | 2/413 |
| 2002/0004120 A1 | 1/2002 | Hillier | 428/73 |
| 2003/0131417 A1 | 7/2003 | Roux | 5/654 |
| 2003/0181990 A1 | 9/2003 | Phillips | 623/37 |
| 2005/0043585 A1 | 2/2005 | Datta et al. | 600/153 |
| 2006/0085919 A1 | 4/2006 | Kramer et al. | 5/713 |
| 2006/0174518 A1 | 8/2006 | Fogarty et al. | 36/61 |
| 2011/0163885 A1 | 7/2011 | Poulos et al. | 340/626 |

OTHER PUBLICATIONS

Convery et al. "Conventional patellar-tendon-bearing (PTB) socket/stump interface dynamic pressure distributions recorded during the prosthetic stance phase of gait of a trans-tibial amputee," Prosthetics and Orthotics International, vol. 22, No. 3, 1998, pp. 193-198.

Hagberg et al., "Consequences of non-vascular trans-femoral amputation: a survey of quality of life, prosthetic use and problems." Prosthetics and Orthotics International, vol. 25, No. 3, 2001, pp. 186-194.

International Preliminary Report on Patentability in International Application No. PCT/US2014/072338 dated Jul. 7, 2016.

International Search Report and Written Opinion in International Application No. PCT/US2014/072338 dated Jun. 2, 2015.

Sanders et al., "Clinical Utility of In-Socket Residual Limb Volume Change Measurement: Case Study Results," Prosthetics and Orthotics International, vol. 33, No. 4, 2009, pp. 378-390.

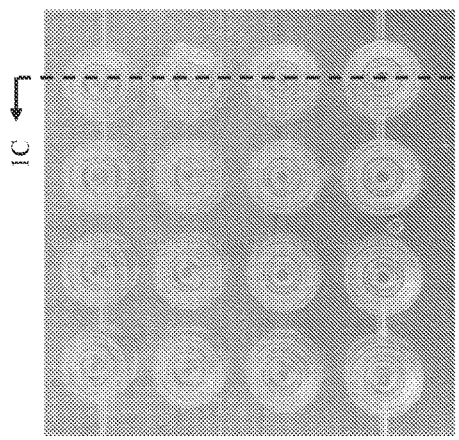
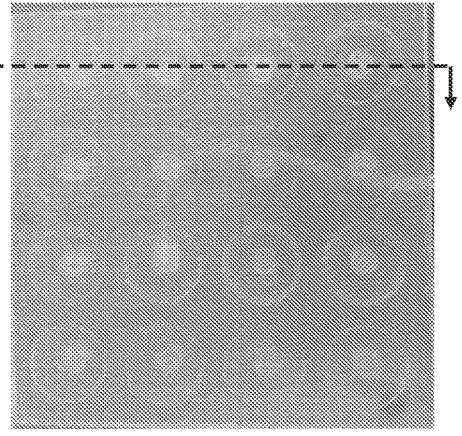
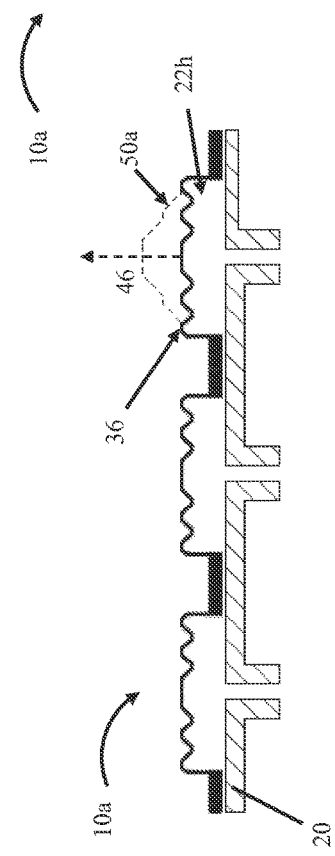
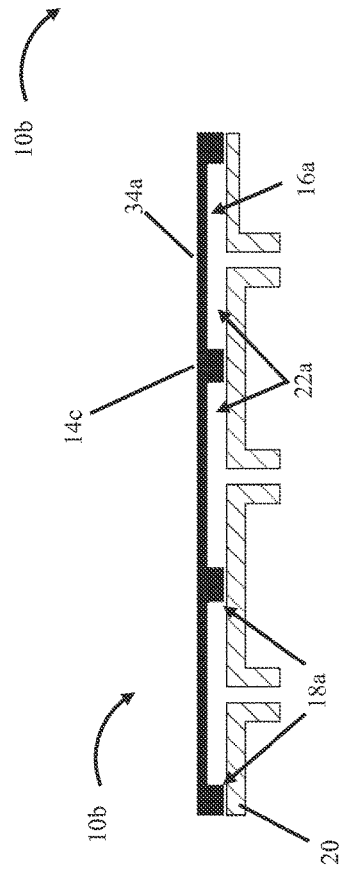

FLUID-DRIVEN BUBBLE ACTUATOR ARRAYS

CROSS-REFERENCE TO RELATED APPLICATIONS

This application is a national phase application under 35 U.S.C. § 371 of International Application No. PCT/US2014/072338, filed Dec. 24, 2014, which claims the benefit of priority of U.S. Provisional Patent Application No. 61/920,903, filed Dec. 26, 2013. The entire contents of each of the above-referenced disclosures are hereby incorporated by reference.

BACKGROUND

1. Field of Invention

The present invention relates generally to apparatuses and methods for dynamic control of surface morphology, and more specifically, but not by way of limitation, to two-dimensional fluid-driven bubble actuator arrays.

2. Description of Related Art

Examples of fluid-driven actuator arrays are disclosed in U.S. Pat. No. 6,092,249; and U.S. Pat. No. 5,267,365.

Devices that require contact with a user's body such as prosthetic limbs, beds, seat cushions, or helmets pose the risk for discomfort and sores, particularly when the user has limited mobility. In almost all of these devices, consistent conformal contact between the device and the human body is desirable for both comfort and safety.

With regards to prosthetic limbs, the volume of a residual limb changes through the gait cycle and throughout the day (Board, W. 2001; Sanders, Harrison et al. 2009). This may be particularly evident in transtibial amputations, as the tissue consistency from anterior to posterior is often markedly different; however, this variation in tissue types exists in transfemoral amputations as well (Convery and Buis 1998). Residual limb volume changes can result in excessive pressures, as well as shear and frictional forces upon a residual limb in a prosthesis socket. If conditions between a residual limb and prosthesis socket are suboptimal, discomfort, skin irritation, and/or pressure ulcers may result. Studies have reported that among non-vascular transfemoral amputees one of the most frequent complaints is sore skin and/or irritation from prosthetic limb sockets. (Hagberg and Branemark 2001).

Current devices and methods designed to ensure fit and comfort for prostheses are generally passive. For example, some amputees place layers of socks over their residual limb before insertion into a prosthesis socket in an attempt to achieve a better fit or to compensate for residual limb volume changes. Additionally, certain systems may use vacuum-assisted prosthesis sockets, and others use air-cushioned sockets. Existing systems, however, are generally incapable of modulating or distributing the pressure exerted on the residual limb or actively compensating for residual limb volume changes.

Prosthetic limb users are not the only individuals susceptible to contact related skin damage. Pressure ulcers may be caused by prolonged contact between a bed or chair and a part of the body. Due to their immobility, stroke patients and individuals with spinal cord injuries may be particularly susceptible to such pressure ulcers.

Currently, safeguards against ulcers include frequent skin examination, body weight shifting, and monitoring of moisture accumulation. Additionally, certain cushions or water beds are available, but these devices still require outside human intervention to frequently move the individual to avoid pressure ulcer formation. Existing methods may be insufficient to prevent pressure ulcers because these methods are not capable of actively modulating or distributing the pressure exerted on the individual. Such existing methods may also require extensive human resources.

Existing methods for impact protection may involve foam cushioning disposed on and/or within a wearable device (e.g., protective gear, such as, for example, helmets, pads, body armor, and/or the like). However, such existing methods may not ensure consistent conformal contact between the wearable device and a user of the wearable device (e.g., existing crash helmets may be unable to ensure consistent conformal contact between an inner surface of the helmet and a user's head and/or may over pressurize some parts of the user's head). Furthermore, current methods may be unable to effectively distribute forces from an impact (e.g., whether spatially and/or temporally) to minimize damage to the user.

Helmets may also be used for cranial remodeling of an infant skull. Plagiocephaly, an asymmetrical distortion of the skull, is a common condition in infants caused by both genetic malformities and external factors. One of the most effective treatments for correcting this asymmetrical distortion is the use of an orthotic helmet. Orthotic helmets apply pressure to the non-deformed section of the head so that the skull grows in the appropriate direction, thereby rounding the head. Currently, the pressure exerted by an orthotic helmet generally cannot be precisely determined. Frequent doctor visits (every one to four weeks for a period of 3 to 6 months) and helmet reconfigurations are required for proper treatment. Existing methods of cranial remodeling are not capable of actively reshaping the skull as it grows or exerting known pressures on the skull as prescribed by a doctor.

Robotic manipulators are typically used to grasp and move objects in a number of degrees of freedom, and are used in a wide variety of applications, including, but not limited to, manufacturing, surgery, human/robot interactions, produce picking, and/or the like, and may be particularly suited to applications in which human presence is dangerous and/or otherwise undesirable (e.g., space operations, working with toxic substances, and/or the like). The successful grasping and/or moving of objects can largely depend on the degree of conformal contact between the object and the manipulator. For example, insufficient conformal contact between the manipulator and the object can result in the object becoming separated from the manipulator during grasping and/or moving, and too strong of a conformal contact can cause damage to the object. Ensuring such adequate conformal contact typically requires precise manipulator movements and/or manipulators specifically designed for interaction with the particular object being manipulated. Depending on the object, this can require the manipulator to be able to move in multiple and complex degrees of freedom. Current robotic manipulators may be capable of conforming to an object that is well-defined (e.g., the material properties and/or shape of the object are known to the robotic manipulator and/or to the robotic manipulator controller). However, for undefined objects or objects that the manipulator has not been designed and/or configured to grasp, the grasping can be suboptimal, which may result in separation of the object from the manipulator and/or damage to the object.

Prosthetic manipulators can function similarly to robotic manipulators, and are typically either myoelectric or switch based. In either type, body movements such as muscle contractions can be used to actuate the prosthetic manipulator. As with robotic manipulators, successful grasping and/or movement of an object may require adequate conformal contact between the manipulator and the object. Current prosthetic manipulators may not be capable of adequately grasping the wide variety of objects a user may wish to interact with, and may require the user to change or adjust the prosthesis. Additionally, fragile, slippery, or objects that are otherwise difficult to grasp may require a degree of precision of manipulator control that current prosthetic manipulators are unable to provide.

SUMMARY

Some embodiments of the present apparatuses and methods use or include a flexible two-dimensional array of fluid-driven bubble actuators. In some embodiments, fluid can be injected into or removed from the bubble actuators in order to cause the surface of the array to change topography and/or stiffness (e.g., to distribute pressure loads and/or impact loads, whether spatially and/or temporally, and/or provide consistent conformal contact between an object such as a part of the human body and the bubble actuator arrays despite changing conditions such as volume changes of a residual limb). Thus, some embodiments of the present apparatuses and methods are configured to dynamically modulate the pressure exerted on an object in contact with the array. The surface of the bubble actuator arrays can be configured to vary based on sensor inputs or based on pre-programmed inputs and/or passively, for example, based upon pressure and/or impact loads applied to the bubble actuator arrays.

Some embodiments of the present apparatuses comprise: a flexible first layer comprising a substantially flat first portion and a plurality of second portions each protruding away from the first portion to define a chamber, a majority of which is surrounded by a boundary lying on the first portion; and a flexible second layer that is substantially flat; where the first layer is sealed in fixed relation to the second layer along the boundaries to define a plurality of cells between the first layer and the second layer in the chambers and such that the first layer has a surface overlying the cells; and the apparatus is configured to be coupled to a fluid source such that the fluid source can deliver fluid to vary internal pressures of the plurality of cells.

Some embodiments of the present apparatuses comprise: a flexible first layer comprising a first side that is substantially flat and a second side having a substantially flat first portion and a plurality of second portions each protruding inward toward the first side to define a recess, a majority of which is surrounded by a boundary lying on the first portion; and a flexible second layer; where the first layer is sealed in fixed relation to the second layer along the boundaries to define a plurality of cells between the first layer and the second layer in the recesses and such that a surface of either the first layer or the second layer overlies the cells; and where the apparatus is configured to be coupled to a fluid source such that the fluid source can deliver fluid to vary internal pressures of the plurality of cells. In some embodiments, a surface of the first layer overlies at least some of the plurality of cells and a surface of the second layer overlies at least some of the plurality of cells.

In some embodiments of the present apparatuses, the first layer comprises a plurality of coupling members protruding from the first portion opposite the second portions, the plurality of coupling members embedded in the second layer. In some embodiments, the second layer is molded around the coupling members of the first layer. In some embodiments, at least one of the first layer and the second layer comprises an elastic material. In some embodiments, at least a portion of at least one of the first layer or second layer has a thickness of 0.25 millimeter (mm) or larger. In some embodiments, at least a portion of the surface is smooth such that cells underlying the smooth portion of the surface are configured to deflect the smooth portion of the surface outwardly in at least a lateral and an axial direction under an increased internal pressure of the cells underlying the smooth portion of the surface. In some embodiments, at least a portion of the surface is corrugated such that cells underlying the corrugated portion of the surface are configured to deflect the corrugated portion of the surface outwardly in a substantially axial direction under an increased internal pressure of the cells underlying the corrugated portion of the surface. In some embodiments, the apparatus is configured such that a maximum displacement of the surface overlying at least one of cells is between 2% and 15% of a transverse dimension of the cell for each pound per square inch (psi) increase in internal pressure between 1 psi and 5 psi.

Some embodiments of the present apparatuses are configured such that an internal pressure in at least one of the plurality of cells can be varied independently of an internal pressure in another one of the plurality of cells. In some embodiments, the apparatus is configured such that an internal pressure in each of the plurality of cells can be varied independently of an internal pressure in each of the others of the plurality of cells. In some embodiments, each of the plurality of cells has a transverse dimension that is substantially equal to a corresponding transverse dimension of the others of the plurality of cells.

In some embodiments of the present apparatuses, at least one of the plurality of cells has a transverse dimension that is different than a corresponding transverse dimension of another one of the plurality of cells. In some embodiments, at least some of the plurality of cells sequentially decrease in size along at least one transverse direction of the flexible layers. In some embodiments, each of the plurality of cells has a transverse dimension of 1 millimeter (mm) or larger. In some embodiments, each cell has a transverse dimension of between 5 millimeters (mm) and 15 mm.

Some embodiments of the present apparatuses comprise a fluid source configured to be coupled to the layers and to vary internal pressures in the plurality of cells.

Some embodiments of the present apparatuses comprise a plurality of sensors coupled to the apparatus and configured to detect one or more physical characteristics. In some embodiments, at least some of the sensors are configured to detect pressure. In some embodiments, at least some of the sensors are configured to detect shear-force. In some embodiments, at least some of the sensors are configured to detect temperature. In some embodiments, at least some of the sensors are configured to detect pH. Some embodiments further comprise a processor configured to control the fluid source to adjust the internal pressure in the plurality of cells at least partly based on data detected by the sensors. Some embodiments further comprise: a memory configured to store pressure patterns; and a processor in communication with the memory and configured to control the fluid source to adjust the internal pressure in the plurality of cells at least partly based on the pressure patterns.

Some embodiments of the present apparatuses are configured to be coupled to a prosthesis socket. In some embodiments, the apparatus is configured to be coupled to a helmet. In some embodiments, the apparatus is configured to be coupled to a prosthetic limb. In some embodiments, the apparatus is configured to be coupled to a bed. In some embodiments, the apparatus is configured to be coupled to a seat.

Some embodiments of the present manipulators comprise at least two opposing grasping members configured to move relative to one another to grasp an object; and one of the present apparatuses disposed on at least one of the grasping members such that the apparatus (e.g., the first layer) will contact an object grasped between the grasping members (e.g., such that fluid can be delivered to the cells to expand the cells and exert a force on the grasped object). In some embodiments, the manipulators further comprise a second one of the present apparatuses. In some embodiments, the first one of the present apparatuses is disposed on a first one of the grasping members and the second one of the present apparatuses is disposed on a second one of the grasping members. In some embodiments, the internal pressures of the plurality of cells of the first one of the present apparatuses can be varied independently of the internal pressures of the plurality of cells of the second one of the present apparatuses.

Some embodiments of the present robotic grippers comprise one of the present manipulators.

Some embodiments of the present prosthetics (e.g., prosthetic hand, foot, arm, and/or leg, and/or the like) comprise one of the present manipulators. Some embodiments further comprise a socket configured to receive a residual limb of a user; and one of the present apparatuses disposed within the socket such that the apparatus will contact the residual limb when the prosthetic arm is worn by the user.

Some embodiments of the present methods comprise: placing an amount of polymer material into a mold configured to form a flexible first comprising a plurality of recesses, each recess having a boundary that surrounds a majority of the recess and a mold configured to form a flexible second layer that is substantially flat; curing the polymer material; extracting a first layer and a second layer from the molds; and bonding the first layer to the second layer.

Some embodiments of the present methods comprise: placing a first amount of polymer material into a first mold piece; coupling a second mold piece to the first mold piece to form a flexible first layer having a substantially flat first portion and a plurality of second portions each protruding away from the first portion to define a chamber a majority of which is surrounded by a boundary lying on the first portion; curing the first amount of polymer material; removing the second mold piece; placing a second amount of polymer material in the first mold piece; coupling a third mold piece to the first mold piece to form a substantially flat second layer adjacent to the first layer and comprising a plurality of fluid passageways; curing the second amount of polymer material; removing the third mold piece from the first mold piece; and extracting the first layer and the second layer from the first mold piece. Some embodiments of the present methods comprise: placing a sacrificial material (e.g., gelatin, wax, and/or sugar) in the chambers of the flexible first layer; and removing, through the plurality of fluid passageways, the sacrificial material from the chambers.

Some embodiments of the present methods further comprise coating the molds with an anti-stiction agent. In some embodiments, the anti-stiction agent is parlyene. In some embodiments, the coating is 1-10 μm thick.

In some embodiments of the present methods, the polymer material comprises RTV-4234-T4. In some embodiments of the present methods, the polymer material comprises polyurethane rubber. In some embodiments of the present methods, the polymer material comprises natural rubber. In some embodiments of the present methods, the polymer material comprises nylon.

Some embodiments of the present methods comprise adjusting with a processor and fluid source an internal pressure of one or more of the plurality of cells in one of the present apparatuses. In some embodiments, the apparatus is in contact with a user.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 1C is a side cross-sectional view of a second embodiment of the present bubble actuator arrays.

FIG. 1D is a top perspective view of the embodiment of FIG. 1C.

FIG. 2A is a side cross-sectional view of a third embodiment of the present bubble actuator arrays.

FIG. 2B is a top perspective view of the embodiment of FIG. 2A.

DETAILED DESCRIPTION OF ILLUSTRATIVE EMBODIMENTS

Figure 1A:
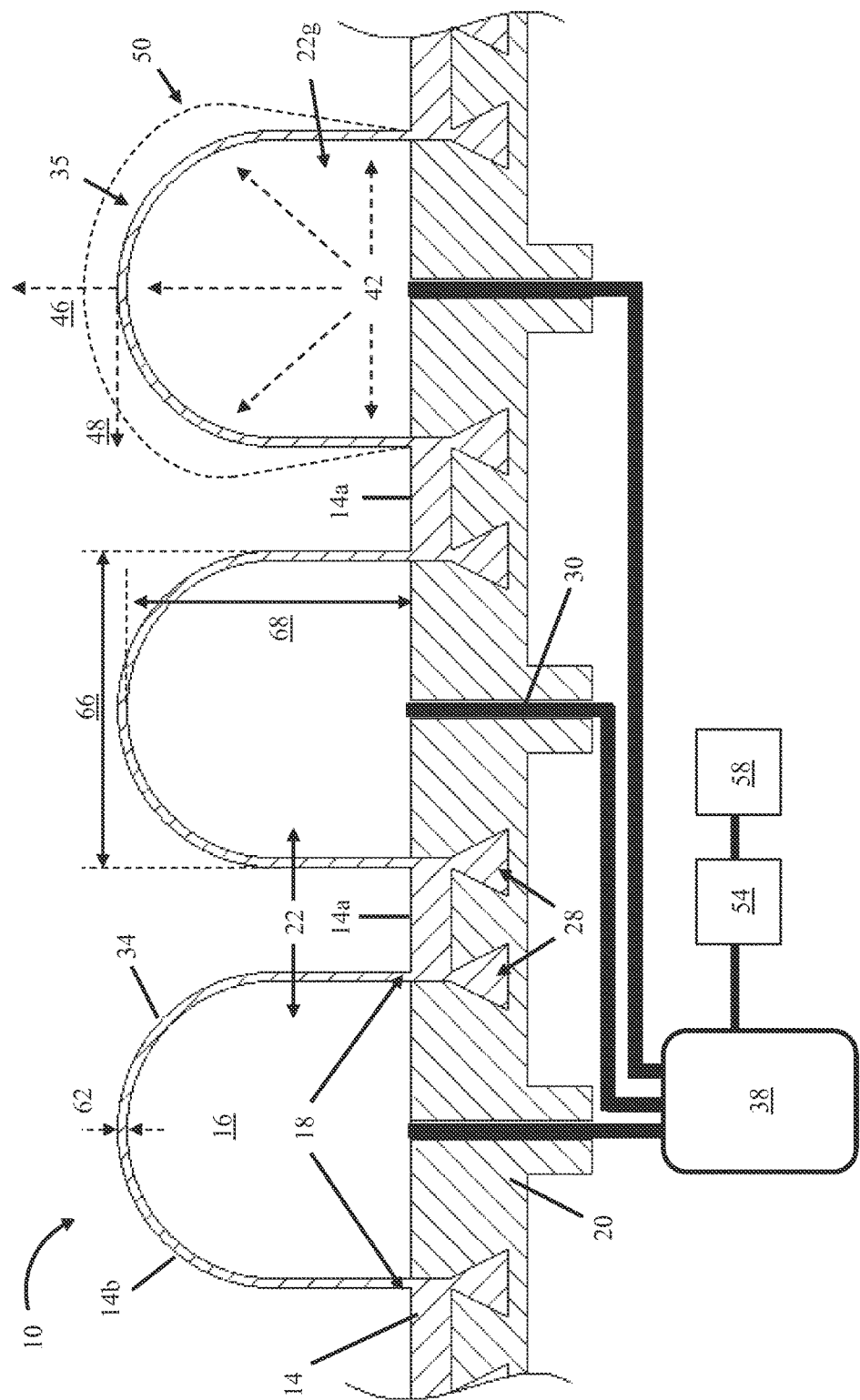
FIG. 1A is a side cross-sectional view of one embodiment of the present bubble actuator arrays.

FIG. 1A shows a cross-sectional view of an embodiment 10 of the present bubble actuator arrays. In the embodiment shown, array 10 comprises a first flexible layer 14 comprising a substantially flat first portion 14a and a plurality of second portions 14b each protruding away from the first portion to define a chamber 16, a majority of which is surrounded by a boundary 18 lying on the first portion.

In the embodiment shown, array 10 further comprises a second flexible layer 20 that is substantially flat. In the embodiment shown, the first layer 14 is sealed in fixed relation to the second layer along boundaries 18 to define a plurality of cells 22 between the first layer and the second layer in chambers 16 and such that the first layer has a surface 34 overlying the cells. In other embodiments, such as array 10b, shown in FIGS. 2A and 2B, and array 10c, shown in FIGS. 2C and 2D, at least one of flexible layers (e.g., 14c or 20) comprises a first side that is substantially flat and a second side having a substantially flat first portion and a plurality of second portions each protruding inward toward the first side to define a plurality of recesses 16a, where each recess has a boundary 18a that surrounds a majority of the recess. In these embodiments, the first layer is sealed in fixed relation to the second layer along the boundaries to define a plurality of cells 22a between the first layer and the second layer in the recesses and such that a surface 34a of the first layer or the second layer overlies the cells (e.g., layer 14c in array 10c has surface 34a which overlies cells 22a). In such embodiments, the arrays comprise a substantially flat surface 34a when cells 22a have an internal pressure (e.g., 42) of nearly ambient pressure (e.g., the cells have an internal pressure substantially equal to the ambient pressure acting on the outside of the cells). In other embodiments, a surface of the first layer can overlie at least some of the plurality of cells and/or a surface of the second layer can overlie at least some of the plurality of cells (e.g., recesses 16a can be located in either or both of the two flexible layers).

Cells (e.g., 22) of the present disclosure can comprise any suitable shape, such as, for example, a shape having a rounded (e.g., circular, elliptical, and/or the like), polygonal (e.g., triangular, rectangular, pentagonal, hexagonal, and/or the like), and/or the like transverse and/or longitudinal cross-section.

Figure 1B:
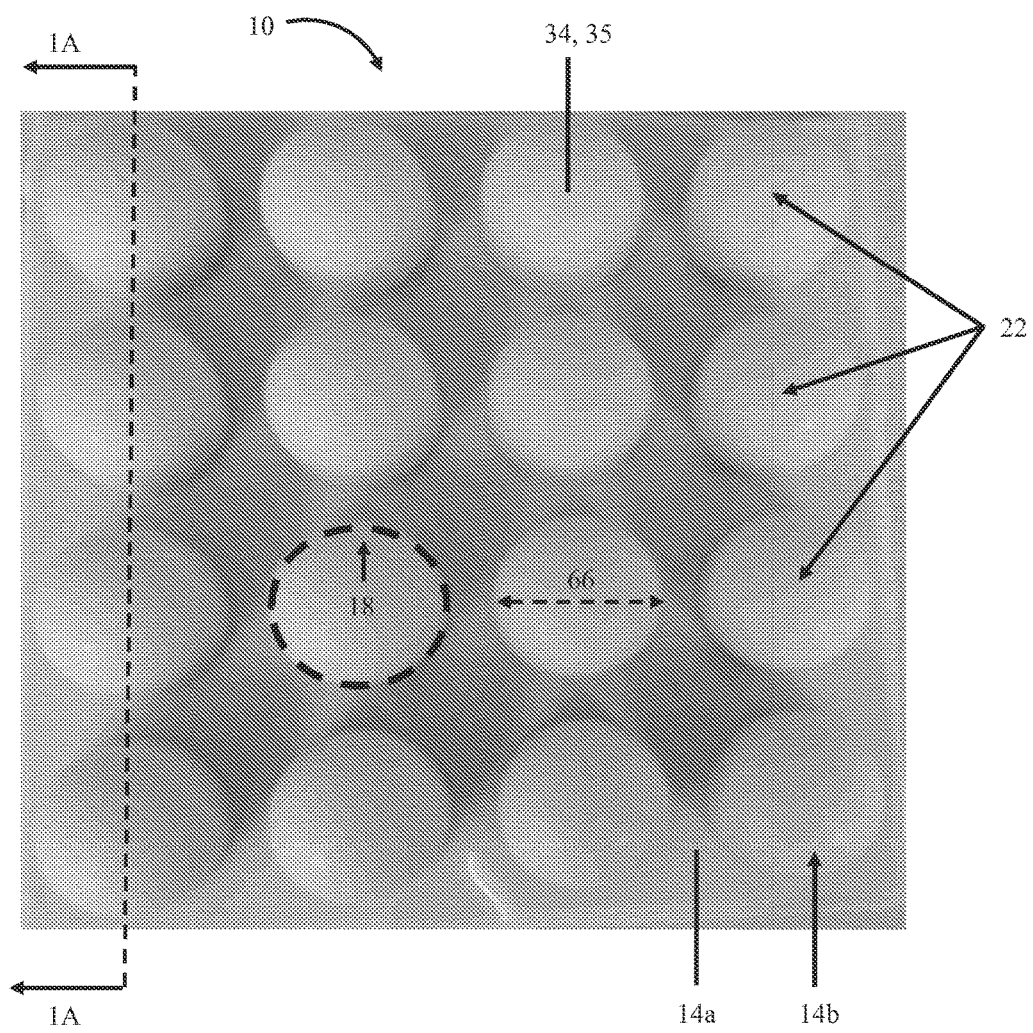
FIG. 1B is a top perspective view of the embodiment of FIG. 1A.

Referring back to FIGS. 1A and 1B, in the embodiment shown, the first layer 14 comprises a plurality of coupling members 28 protruding from the first portion 14a opposite the second portions 14b, the plurality of coupling members embedded in the second layer 20. In the embodiment shown, the second layer is molded around the coupling members of the first layer. In other embodiments, the first layer can be sealed to the second layer in any manner which permits the functionality described in this disclosure, including, but not limited to, through oxygen plasma activation, adhesive, melting, fasteners, and/or the like.

In the embodiment shown, array 10 comprises a plurality of fluid passageways 30 in fluid communication with cells 22 such that fluid can be delivered to or removed from cells 22 via passageways 30. The present arrays can be used with any suitable fluid, such as, for example, air, water, Newtonian fluids, non-Newtonian fluids, and/or the like. In this embodiment each cell has a dedicated passageway 30 such that fluid can be delivered to or removed from each cell 22 individually. In other embodiments, multiple cells 22 can be in fluid communication with each other via passageways 30 such that fluid can be delivered to or removed from each of a plurality of groups (each including a plurality) of cells 22 independently (e.g., array 10c). In the embodiment shown, boundary 18 is not interrupted for fluid passageways 30 which instead pass through second layer 20; however, in other embodiments, boundary 18 may be interrupted by fluid passageways passing between layers 14 and 20 but still be continuous around a majority of the perimeter of each cell such that boundary 18 still defines each cell 22. In such embodiments, the present bubble actuator arrays can be configured to deflect surfaces (e.g., 34) of both first and second layers under applied internal cell pressures (e.g., 42).

In the embodiment shown, array 10 is configured to be coupled to a fluid source 38, such that the fluid source can deliver fluid to vary internal pressures (e.g., positive internal pressure indicated by arrows 42) of cells 22 (e.g., individually and/or collectively), such as by delivering fluid to the cells through fluid passageways 30. In some embodiments, such as the one shown, each cell 22 is configured to be capable of producing a large surface deflection of surface 34 (e.g., in direction 48 and/or direction 46 to an outwardly deflected position 50) and/or to apply a large force (e.g., in the direction indicated by arrow 46) to an object in contact with surface 34 through pressurization (e.g., as indicated by arrows 42) of some or all of cells 22 and/or deformation of the surface 34 corresponding to the pressurized cells (e.g., in direction 48 and/or direction 46) caused by the delivery of fluid to the pressurized cells. In some embodiments, fluid can be moved between cells (e.g., 22) passively (e.g., without requiring operation of fluid source 38). For example, in some embodiments, deformation of one cell may cause fluid to communicate from the cell to one or more others of the cells, for example, via shared fluid passageway(s) 30 (e.g., and any given cell may be interconnected with any number of other cells via any number of shared fluid passageway(s)). Such passive fluid movement amongst the cells can be adjusted, for example, by varying the thickness (e.g., 62) of layers that at least partially define the cells, cell transverse dimensions (e.g., 66), configuration of shared fluid passageways (e.g., 30), and/or the like. In these and similar embodiments, cells (e.g., 22), fluid passageways (e.g., 30), and/or the like may be filled with a fluid. In some such embodiments, fluid source 38 may be omitted.

Some embodiments of the present apparatuses (e.g., actuators including an embodiment of the present bubble actuator arrays) and systems comprise a fluid source 38 that is configured to be coupled to the array (e.g., 10) (e.g., to cells 22 via fluid passageways 30) such that the fluid source can deliver fluid to and/or remove fluid from the cells to vary internal pressures (e.g., 42) in the cells. Unless otherwise indicated by the context of its use, the term "pressure" includes, but is not limited to, positive pressures, negative (vacuum) pressures, and zero (ambient) pressures, all relative to an ambient (e.g., atmospheric) pressure.

In the embodiment shown, array 10 further comprises a processor 54 that is configured to control fluid source 38 to adjust the internal pressures (e.g., 42) in the plurality of cells. In this embodiment, array 10 also comprises memory 58 in communication with processor 54, the memory configured to store information about actuation of fluid source 38 and/or predefined pressure patterns for actuation of array 10 (e.g., sequential pressurization of cells 22 individually or in groups). In some embodiments pressure patterns can include desired internal pressures (e.g., 42) in at least some of the plurality of cells (e.g., 5 pounds per square inch (psi) of internal pressure in at least one cell). In some embodiments, pressure patterns can include desired measured pressures between the surface (e.g., 34) and an object (e.g., 74), as described in more detail below with reference to FIG. 4. In these embodiments, the processor can be configured to control the fluid source to adjust the internal pressure in the plurality of cells at least partly based on the pressure patterns. Such components and features can further facilitate modulation of pressure levels at various points along the surface (e.g., 34). Unless otherwise indicated by the context of its use, the terms "a processor" or "the processor" mean one or more processors and may include multiple processors configured to work together to perform a function.

In some embodiments, at least one of the first layer and the second layer comprises an elastic material. For example, in the embodiment shown, first layer 14 comprises an elastic material (e.g., rubber, polymer, silicone, and/or the like) such that the first layer can deflect when cells 22 are pressurized and surface 34 can expand elastically (e.g., to a position 50) and return to the pre-expanded state when cells 22 are depressurized. In some embodiments, at least a portion of at least one of the first layer or second layer has a thickness 62 of 0.25 millimeter (mm) or larger (e.g., greater than any one of, or between any two of: 0.25, 0.5, 1, 1.5, 2, 5, 10, 15, 25, and/or 50 mm). In some embodiments, at least a portion of at least one of the first layer or second layer has a thickness 62 of between 0.25 mm and 50 mm. For example, in the embodiment shown, the first layer 14 has a thickness 62 of between 0.5 mm and 1.5 mm. Through selection of layer thickness 62, finer control can be had over surface stiffness and/or topography under desired ranges of applied internal cell pressures (e.g., 42) for particular implementations of the present arrays. For example, increases in first layer thickness may increase first layer stiffness and thereby decrease deflection of surface 34 for a given internal cell pressure.

In the embodiment shown, at least a portion of the surface is smooth such that cells underlying the smooth portion of the surface 35 (e.g., cell 22g) are configured to deflect the smooth portion of the surface 35 outwardly in at least a lateral direction (e.g., 48) and an axial direction (e.g., 46) under an increased internal pressure (e.g., 42) of the cells underlying the smooth portion of the surface (e.g., for a resulting smooth surface 35 displacement 50). In other embodiments, such as array 10a shown in FIGS. 1C and 1D, at least a portion of the surface is corrugated, such that cells underlying the corrugated portion of the surface 36 (e.g., cell 22h) are configured to deflect the corrugated portion 36 of the surface outwardly in a substantially axial direction (e.g., the direction indicated by arrow 46) under an increased internal pressure (e.g., 42) of the cells underlying the corrugated portion of the surface (e.g., for a resulting corrugated surface 36 displacement 50a). Such features of the surface 34 can be selected and/or configured to affect the performance of the present bubble actuator arrays.

Referring back to FIGS. 1A and 1B, in the embodiment shown, each of cells 22 has a transverse dimension 66 of 1 millimeter (mm) or larger (e.g., greater than any one of, or between any two of: 0.25, 0.5, 1, 1.5, 2, 5, 10, 15, 25, 50, 75, 100, 150, 200, 250, 300, and/or 350 mm), such as, for example, between 1.5 mm and 15 mm. In some embodiments, each of cells 22 has a transverse dimension 66 of 50 mm or smaller. In the embodiment shown, each of cells 22 has a transverse dimension 66 that is substantially equal to a corresponding transverse dimension of the others of the plurality of cells: cells 22 are substantially the same size. In other embodiments, at least one of the plurality of cells 22 has a transverse dimension 66 that is different than a corresponding transverse dimension of another one of the plurality of cells (e.g., array 10c). Cells (e.g., 22) of the present disclosure can have any suitable height (e.g., 68) (e.g., which may be measured when an internal pressure of the cell is substantially equal to an ambient pressure), such as, for example, greater than any one of, or between any two of: 0.25, 0.5, 1, 1.5, 2, 5, 10, 15, 25, 50, 75, 100, 150, 200, 250, 300, and/or 350 mm.

Figure 2C:
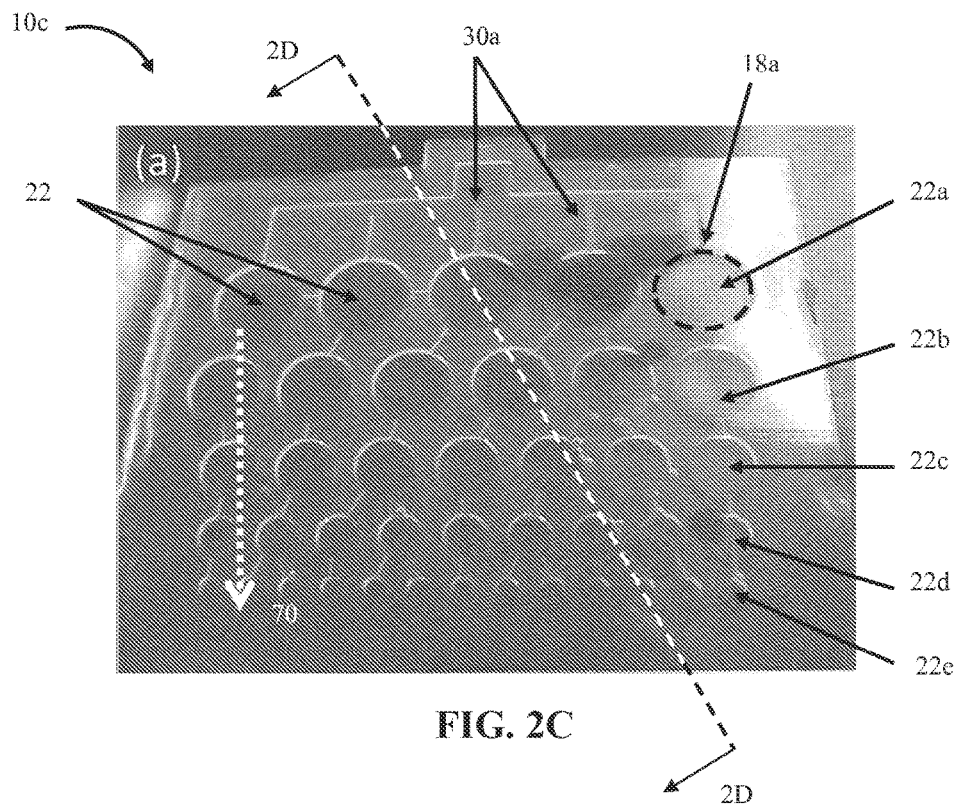
FIG. 2C is a top perspective view of a fourth embodiment of the present bubble actuator arrays.
Figure 2D:
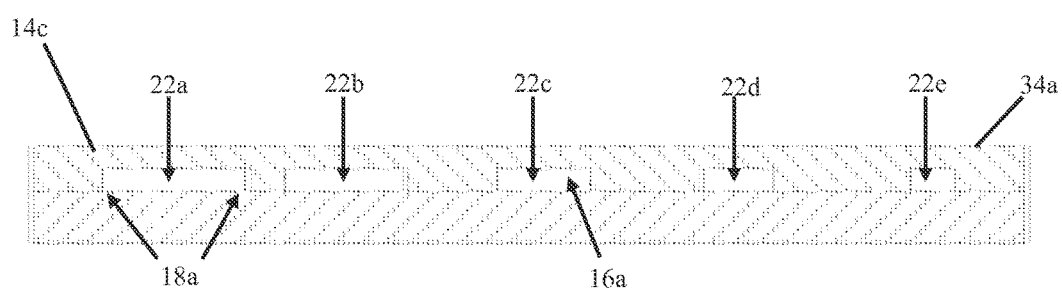
FIG. 2D is a side cross-sectional view of the embodiment of FIG. 2C.

FIGS. 2C and 2D depict a fourth embodiment 10c of the present bubble actuator arrays. Array 10c is substantially similar to array 10b with the primary exception that the cells (22a, 22b, 22c, 22d, and 22e) of array 10c have different sizes, and fluid passageways 30a of array 10c are configured such that groups of cells (e.g., cells 22a, 22b, 22c, 22d, and 22e) are in fluid communication with each other such that fluid can be delivered to and/or removed from groups of cells (each group including a plurality of cells). In this embodiment, an internal pressure (e.g., 42) in at least one of the plurality of cells 22 can be varied independently of an internal pressure in another one of the plurality of cells (e.g., via fluid passageways 30a coupling at least two cells 22 together). In other embodiments, such as array 10 depicted in FIGS. 1A and 1B, the present bubble actuator arrays are configured such that an internal pressure in each of the plurality of cells can be varied independently of an internal pressure in each of the others of the plurality of cells (e.g., through a dedicated fluid passageway 30 for each cell 22).

In some embodiments, at least some of the plurality of cells sequentially decrease in size along at least one transverse direction. For example, in the embodiment shown, the cells decrease in size in direction 70. In particular, cells 22b are smaller than cells 22a, cells 22c are smaller than cells 22b, cells 22d are smaller than cells 22c, and cells 22e are smaller than cells 22d. As with array 10b, the cells of array 10c have a transverse dimension (e.g., diameter) of 50 mm or smaller. In the embodiment shown, cells 22a have a diameter of 10 mm, cells 22b have a diameter of 8 mm, cells 22c have a diameter of 6 mm, cells 22d have a diameter of 4 mm, and cells 22e have a diameter of 2 mm (e.g., each cell 22 of array 10c has a transverse dimension of between 5 mm and 15 mm, and larger than 1 mm).

Figure 3:
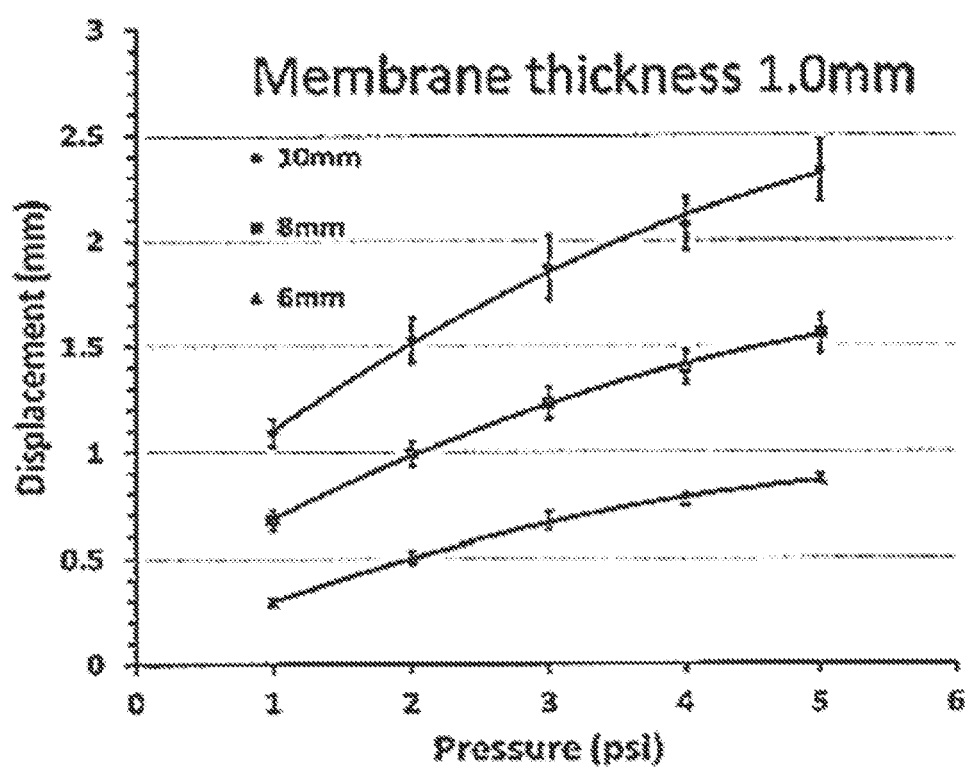
FIG. 3 is a graph showing surface displacement versus internal cell pressure for certain embodiments of the present bubble actuator arrays.

FIG. 3 shows a graph of surface displacement (e.g., deflection 50 measured in direction 46, as illustrated in FIG. 1A) relative to internal cell pressure (e.g., 42) for a first layer thickness 62 of 1 mm. For this graph, the cells (e.g., 22) have circular shapes and transverse dimensions (diameters) 66 of 6 mm, 8 mm, and 10 mm respectively. As shown, variations in cell transverse dimension can affect surface displacement of the cell surface for given internal cell pressures (e.g., 42). As indicated in the graph, some embodiments of the present bubble actuator arrays are configured such that the displacement of the plurality of cells (e.g., each of the plurality of cells 22) can be governed by at least the internal pressure (e.g., 42), the transverse dimension (e.g., 66), and/or the layer thickness (e.g., 62). For example, for the embodiments represented in FIG. 3, a maximum surface displacement for each of the plurality of cells (e.g., 22) is between 2% and 15% of transverse dimension (e.g., 66) of the cell for each pound per square inch (psi) increase in internal pressure (e.g., 42) between 1 psi and 5 psi. Other embodiments of the present bubble actuator arrays can be configured such that a maximum surface displacement for each of the plurality of cells (e.g., 22) is as large as 50 mm under internal pressures (e.g., 42) as high as 50 psi. Through selection of such components and features, embodiments of bubble actuator arrays can be configured to obtain a desired range of surface (e.g., 34) displacements. For example, layer thickness, cell size, and/or cell shape can be selected (e.g., based on clinical data and/or desired performance characteristics) for a given application. As a further example, in some embodiments (e.g., array 10c), cells of different sizes can be in communication with each other such that a common pressure level produces varying deflections for different ones of the cells.

Figure 4:
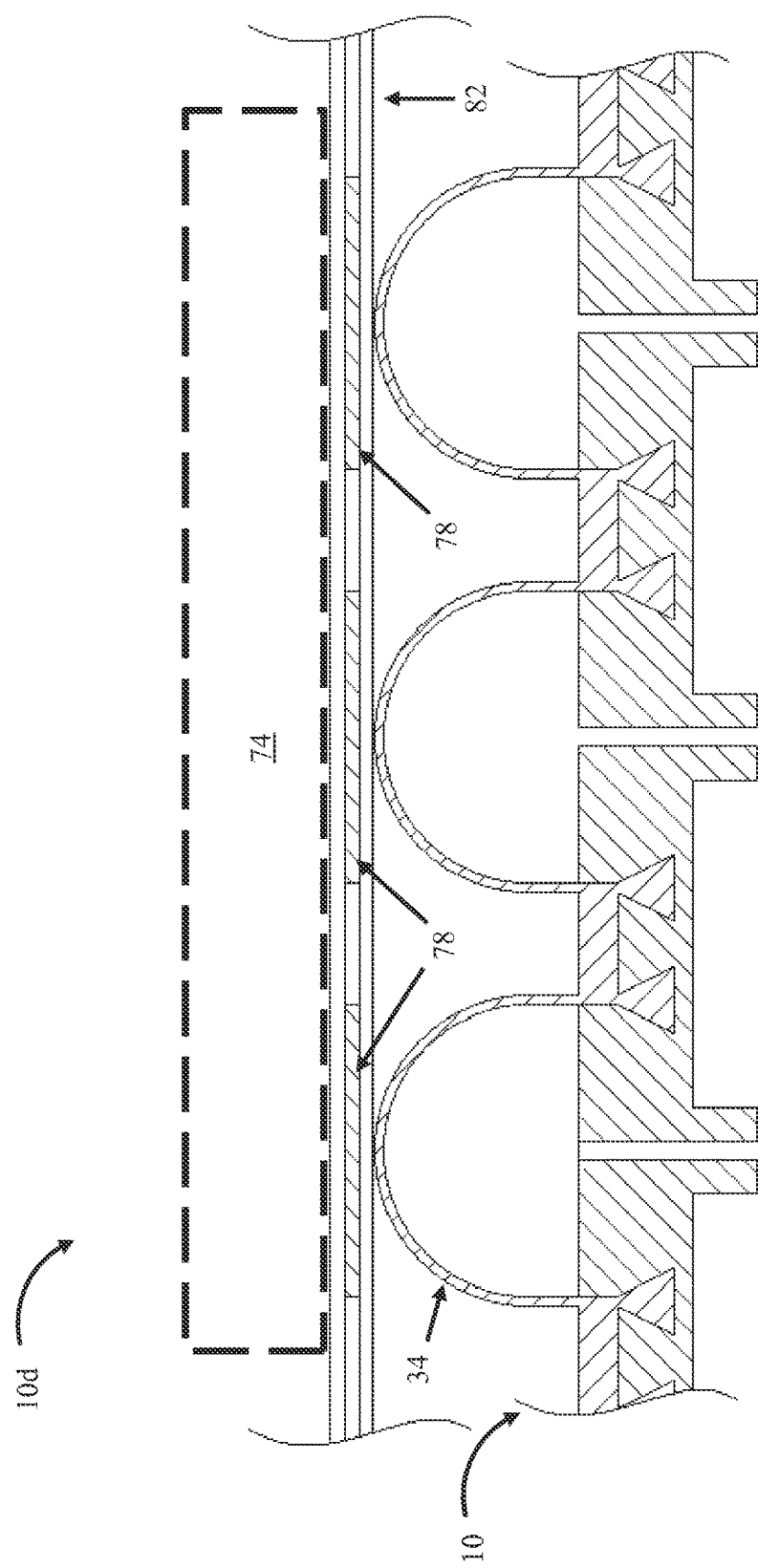
FIG. 4 is a side cross-sectional view of a fifth embodiment of the present bubble actuator arrays that includes a plurality of sensors.

FIG. 4 depicts a fifth embodiment 10d of the present bubble actuator arrays. Array 10d is substantially similar to array 10, with the primary exception that array 10d further comprises a plurality of sensors 78 coupled to array 10 that are be configured to detect one or more physical characteristics. In some embodiments, for example, the physical characteristic(s) that the sensors are configured to detect can be indicative of conditions between surface 34 and an object 74 in contact with a surface (e.g., a person). Sensors 78 can, for example, be configured to detect one or more of pressure, shear-force, temperature, pH, and/or other characteristics. Various suitable sensors are commercially available from a variety of sources, such as, Tekscan, Inc., Vishay Precision Group, Inc., and/or Interlink Electronics. In the embodiment shown, sensors 78 are coupled to a flexible polymeric substrate 82. In other embodiments, sensors 78 may be disposed at any suitable location, such as, for example, coupled directly to surface 34 (without substrate 82), disposed such that the bubble actuator array (e.g., or cells 22 thereof) lies between sensors 78 and an object 74 (e.g., coupled to second flexible layer 20), disposed within fluid passageway(s) 30, and/or the like. While not additionally shown in FIG. 4, as with array 10, array 10d can be coupled to and/or comprise a fluid source 38, a processor 54, and/or memory 58. In such embodiments, processor 54 can be configured to control fluid source 38 to adjust the internal pressure (e.g., 42) in the plurality of cells 22 at least partly based on data detected by sensors 78. In such embodiments, array 10d can operate as a closed-loop system in which:

processor 54 autonomously monitors the pressure and shear-forces between an object (e.g., 74) and surface 34 in real-time (e.g., via sensors 78) and adjusts the pressure and shear forces by changing the internal pressure of the cells (e.g., until data detected by sensors 78 corresponds to pressure patterns stored in memory 58).

This functionality can facilitate compensation for changing conditions between an object (e.g., 74) and the surface 34. In this embodiment, pressure patterns (as described generally above with reference to FIG. 1A) can include desired measured pressures between surface 34 and an object (e.g., 74), such as may be measured by sensors 78 (e.g., 5 psi of pressure between the surface and an object as measured by at least one sensor). Pressure patterns can also include threshold values corresponding to at least one location (e.g., no more than 20 psi of pressure between the surface and an object as measured by at least one sensor). In other embodiments, the processor may adjust the pressure and shear forces exerted by surface 34 on an object 74 to account for moisture accumulation, pH, and/or the like (e.g., a location between the surface and a human body with excessive moisture may require less pressure than dry locations to avoid discomfort and/or sore formation).

Figure 5:
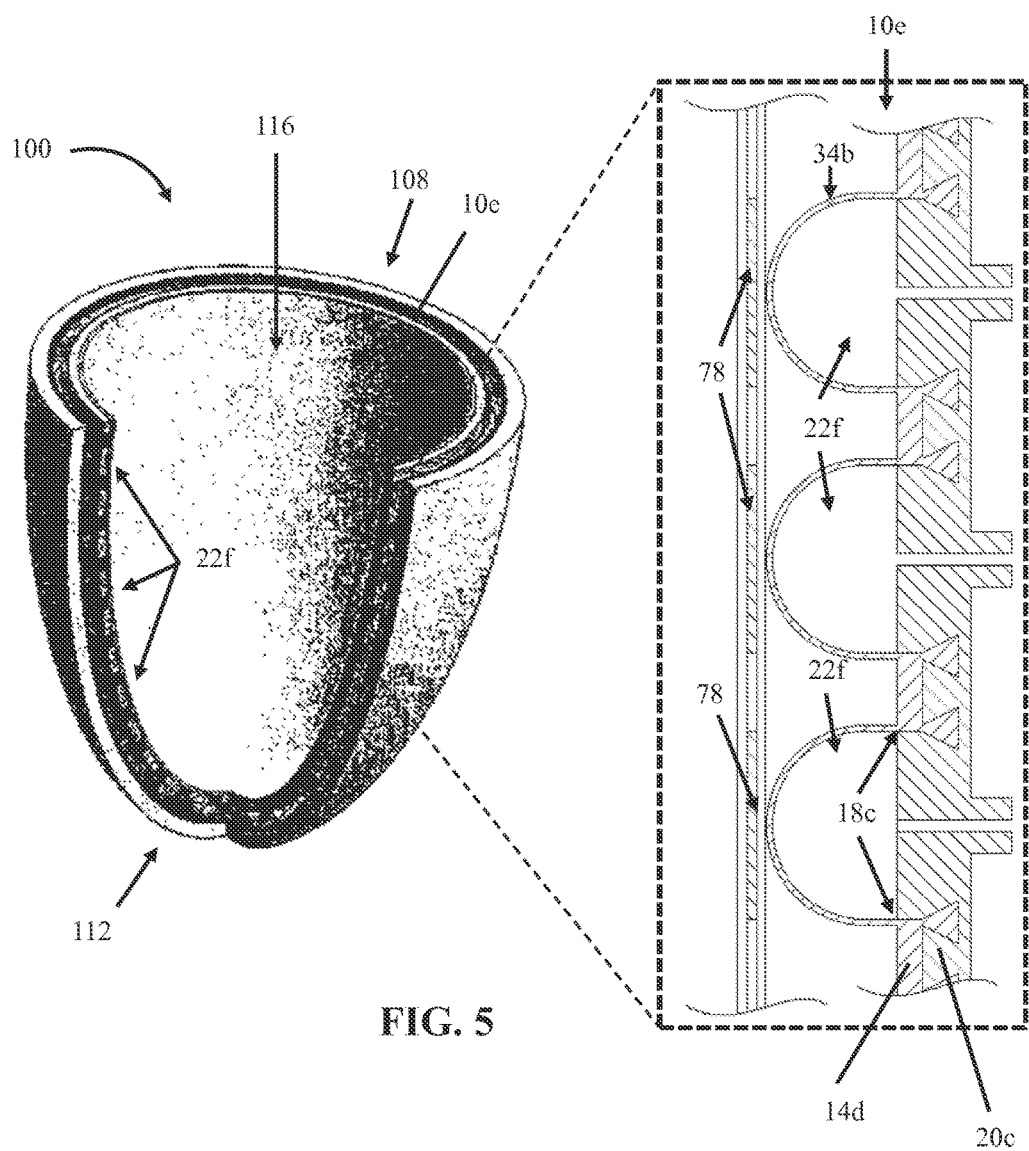
FIG. 5 is a cutaway perspective view of a sixth embodiment of the present bubble actuator arrays that is configured to be coupled to a prosthesis socket.

In some embodiments, the present bubble actuator arrays (e.g., surface 34) can be configured to be coupled to a device that, in use, contacts a user's body. For example, FIG. 5 depicts a perspective view of a prosthetic socket liner 100 comprising a sixth embodiment 10e of the present bubble actuator arrays. Array 10e is substantially similar to array 10d with the primary exception that array 10e is coupled (e.g., through fasteners, adhesive, and/or the like) and contoured to an interior surface of prosthetic socket liner 100 such that array 10e can be actuated to adjust the interface between a prosthetic socket and a user's residual limb (e.g., to precisely control the pressure exerted on each portion of a user's residual limb contacted by liner 100). In some embodiments, a prosthetic socket or a prosthetic socket liner (e.g., 100) may be configured to be coupled to a source of vacuum (e.g., which may be the same as or different than a fluid source 38) (e.g., to enhance the fit of the prosthetic socket, prosthetic socket liner and/or the like on the user's residual limb).

As with array 10d, in the embodiment shown, array 10e includes a plurality of sensors 78 coupled to surface 34b and configured to detect one or more physical characteristics to facilitate monitoring and controlling the pressure and shear-forces of the prosthetic socket environment in real-time. For example, sensors 78 can be configured to record data indicative of the conditions between the residual limb of a user and the prosthetic socket. This data can be communicated to a processor (e.g., 54), which can be further configured to adjust the stiffness and/or contour of the surface 34b through the operation of a controllable fluid source (e.g., 38) that is coupled to cells 22f. Such embodiments can compensate for pressure changes in the socket environment (e.g., due to ambulation and volume changes of a residual limb) to at least ensure an adequate fit and/or decrease shear and frictional forces on the skin of a residual limb, thus reducing the risk of skin irritation or sores. In the embodiment shown, cells 22f are ring-shaped, for example, liner 100 is a cupshaped liner with an open proximal end 108 and a closed distal end 112 which defines an interior volume 116, where first flexible layer 14d (substantially similar to layer 14 in embodiment 10) is sealed to second flexible layer 20c at boundaries 18c to define a plurality of ring-shaped cells 22f between the first layer and the second layer and around volume 116.

Figure 6:
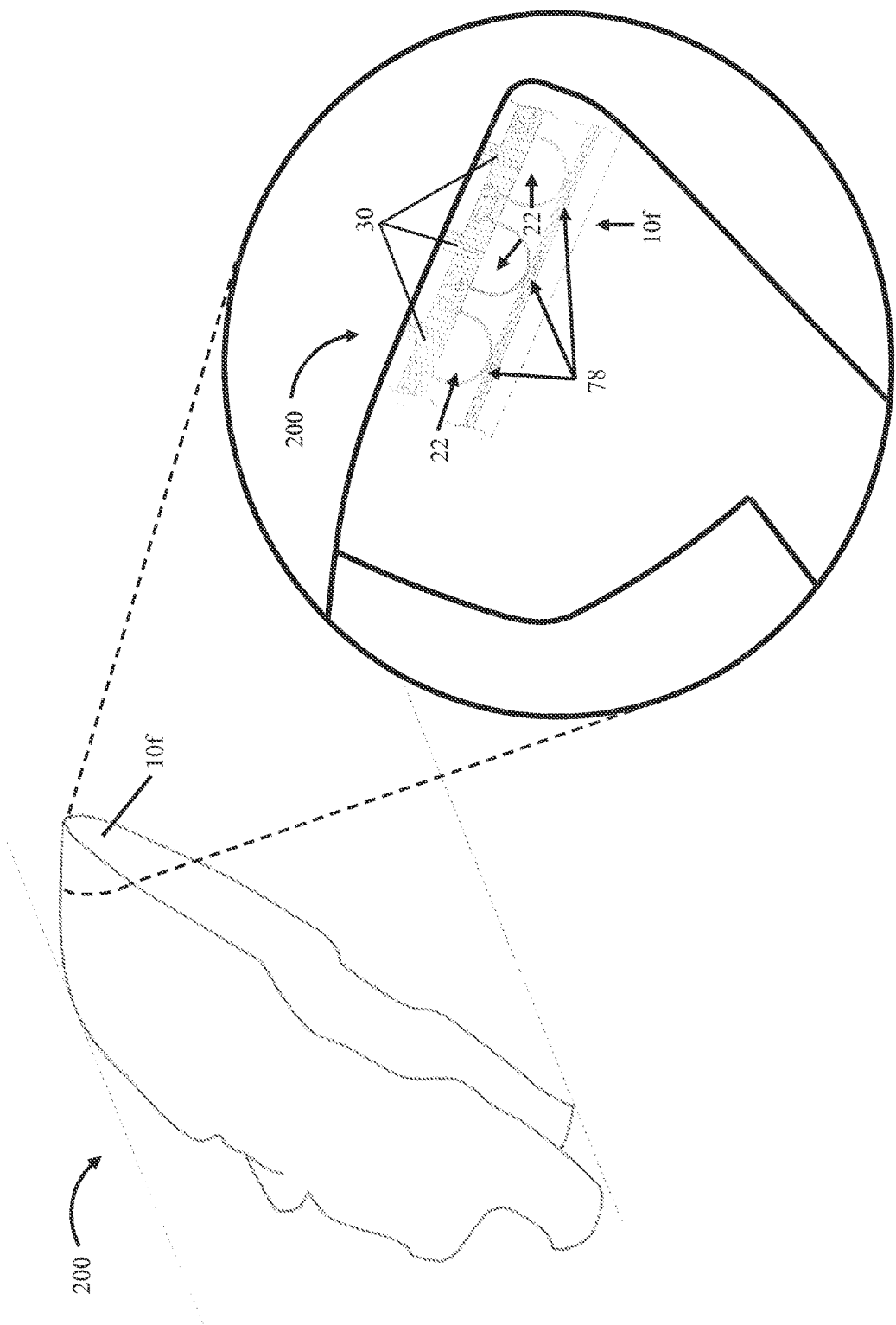
FIG. 6 is a perspective view of a mask that comprises a seventh embodiment of the present bubble actuator arrays.

FIG. 6 depicts a perspective view of a mask 200 comprising a seventh embodiment 10f of the present bubble actuator arrays. Array 10f is substantially similar to array 10d with the primary exception that array 10f is coupled (e.g., through fasteners, adhesive, and/or the like) and contoured to an interior surface of mask 200 such that array 10f can be actuated to adjust the interface between mask 200 and a user's face (e.g., to precisely control the pressure exerted on each portion of a user's face contacted by mask 200). As described above for array 10e, array 10f can be configured with sensors (e.g., 78) and a processor (e.g., 54) to be capable of operating in a closed-loop process to ensure intimate contact between mask 200 and a user's face. For example, the sensors can be configured to monitor the pressure exerted on different contacted parts of the user's face by mask 200. A targeted surface pressure value can be maintained by a processor (e.g., 54) by varying the internal pressures (e.g., 42) in cells 22, and thus the deflections (e.g., 50), of a plurality of cells (e.g., 22) through control of a fluid source (e.g., 38) coupled to the plurality of cells (e.g., through fluid passageways 30). This embodiment is thus configured and can be used to ensure conformal contact between a user's face (e.g., to ensure consistent pressure across a skin graft for a patient with severe facial burns).

Figure 7A:
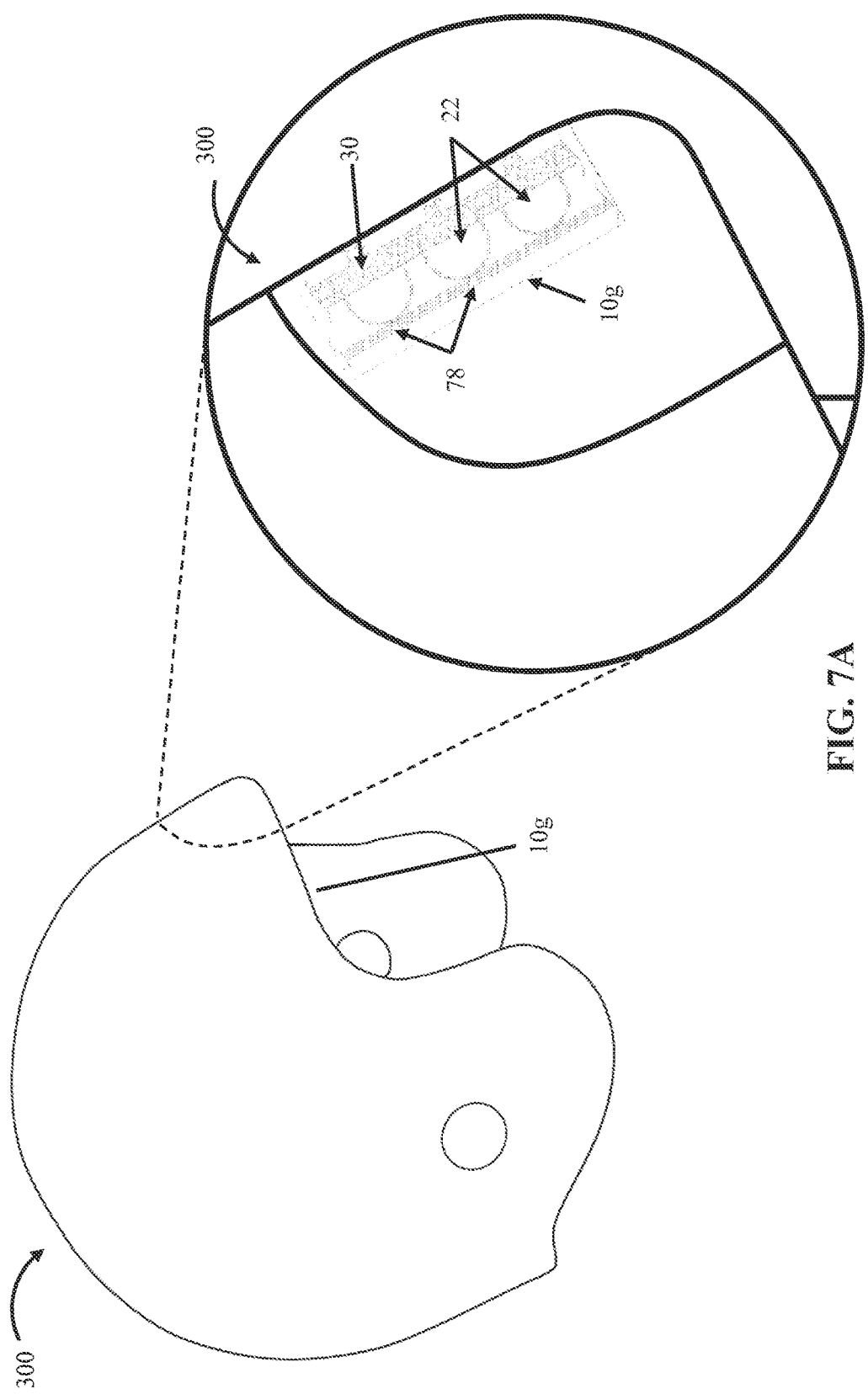
FIG. 7A is a perspective view of a helmet that comprises an eighth embodiment of the present bubble actuator arrays.

FIG. 7A depicts a helmet 300 (e.g., a helmet to be worn during a sporting activity or an orthotic helmet) comprising an eighth embodiment 10g of the present bubble actuator arrays. Array 10g is substantially similar to array 10d with the primary exception that array 10g is coupled (e.g., through fasteners, adhesive, and/or the like) and contoured to an interior surface of helmet 300 such that array 10g can be actuated to adjust the interface between the helmet and a wearers head and thereby encourage conformal contact between the head and the helmet regardless of the shape or contour of the user's head, as well as distribute forces in stages in the event of impact in order to minimize damage to the head. In embodiments in which helmet 300 is an orthotic helmet, array 10g can facilitate application of known pressures to portions of the head of an infant as prescribed by a doctor (e.g., through pressure patterns stored in memory 58) to re-shape the skull. In some embodiments, the pressure exerted by array 10g can be dynamically adjusted as the skull changes shape without having to change or reconfigure the orthotic helmet.

Figure 7B:
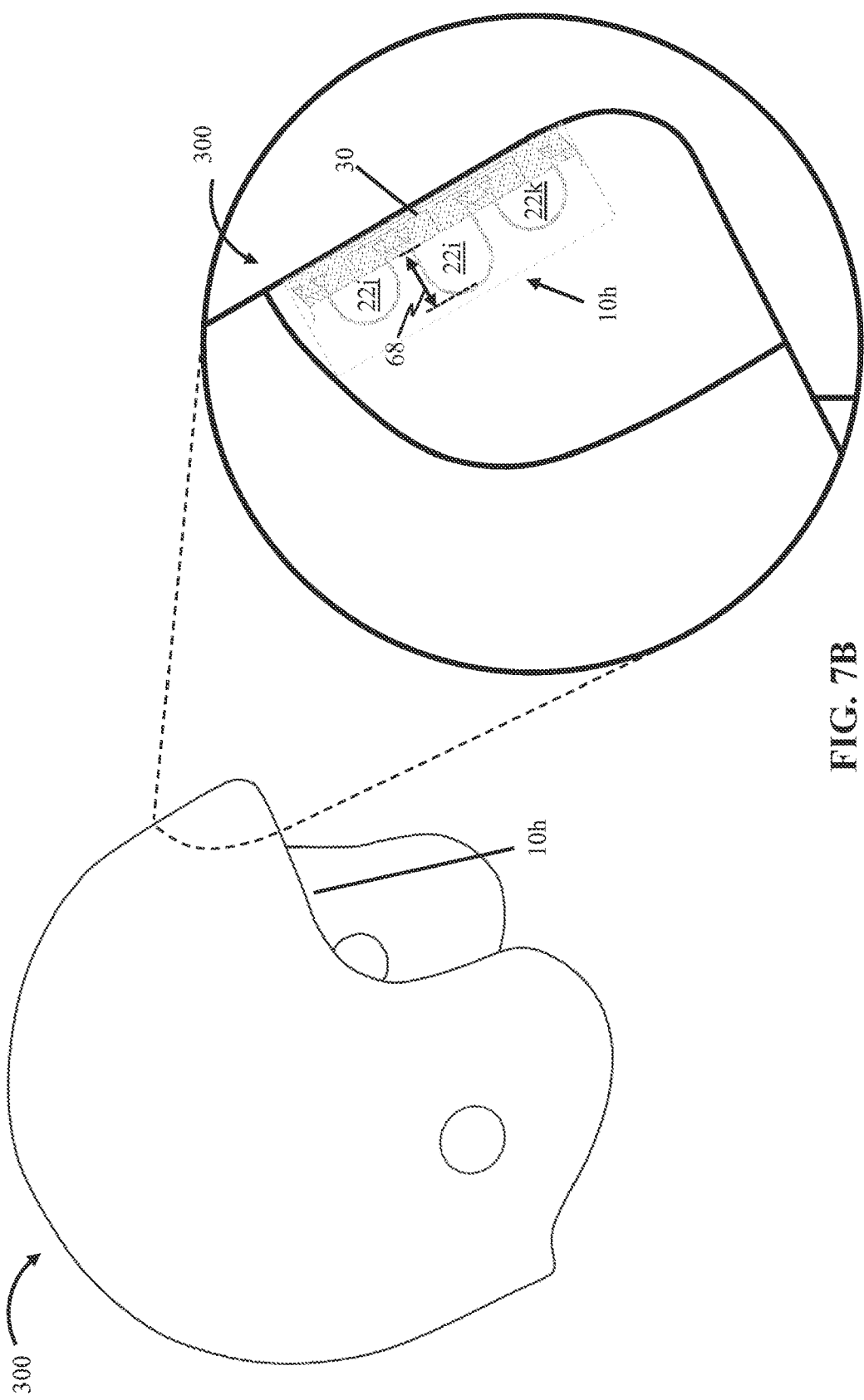
FIG. 7B is a perspective view of a helmet that comprises a ninth embodiment of the present bubble actuator arrays.

FIG. 7B depicts a helmet 300 comprising a ninth embodiment 10h of the present bubble actuator arrays. Array 10h is substantially similar to array 10g, with certain exceptions described below. As described above, in some embodiments of the present arrays (e.g., 10h), fluid can be moved between cells (e.g., 22) passively (e.g., without requiring operation of a fluid source 38) (e.g., deformation of one cell may cause fluid to communicate from the cell to another one of the cells, for example, via a shared fluid passageway 30). For example, in this embodiment, cells 22i, 22j, and 22k share (e.g., are in fluid communication with one another via) a fluid passageway 30, such that, for example, deformation of cell 22i may cause fluid to communicate from cell 22i and to cells 22j and/or 22k.

Such passive fluid movement amongst the cells can be adjusted, for example, by varying the thickness (e.g., 62) of layers that at least partially define the cells, cell transverse dimensions (e.g., 66), cell heights (e.g., 68), configuration of shared fluid passageways (e.g., 30), and/or the like. For example, in this embodiment, cell 22i has a cell height 68 that is larger than a cell height of cell 22j or cell 22k. In this way, for example, in the event of an impact, a user's head within helmet 300 may deform cell 22i before and/or to a larger degree than cells 22j and 22k, which may cause pressurization of cells 22j and 22k (e.g., via fluid communication from cell 22i via fluid passageway 30) (e.g., progressively transmitting (e.g., in stages) and/or redirecting an impact to the user's head, thus reducing a magnitude of impact force experienced by the user). In array 10h and similar arrays, fluid source 38, processor 54, memory 58, sensor(s) 78, and/or the like may be omitted.

Figure 8:
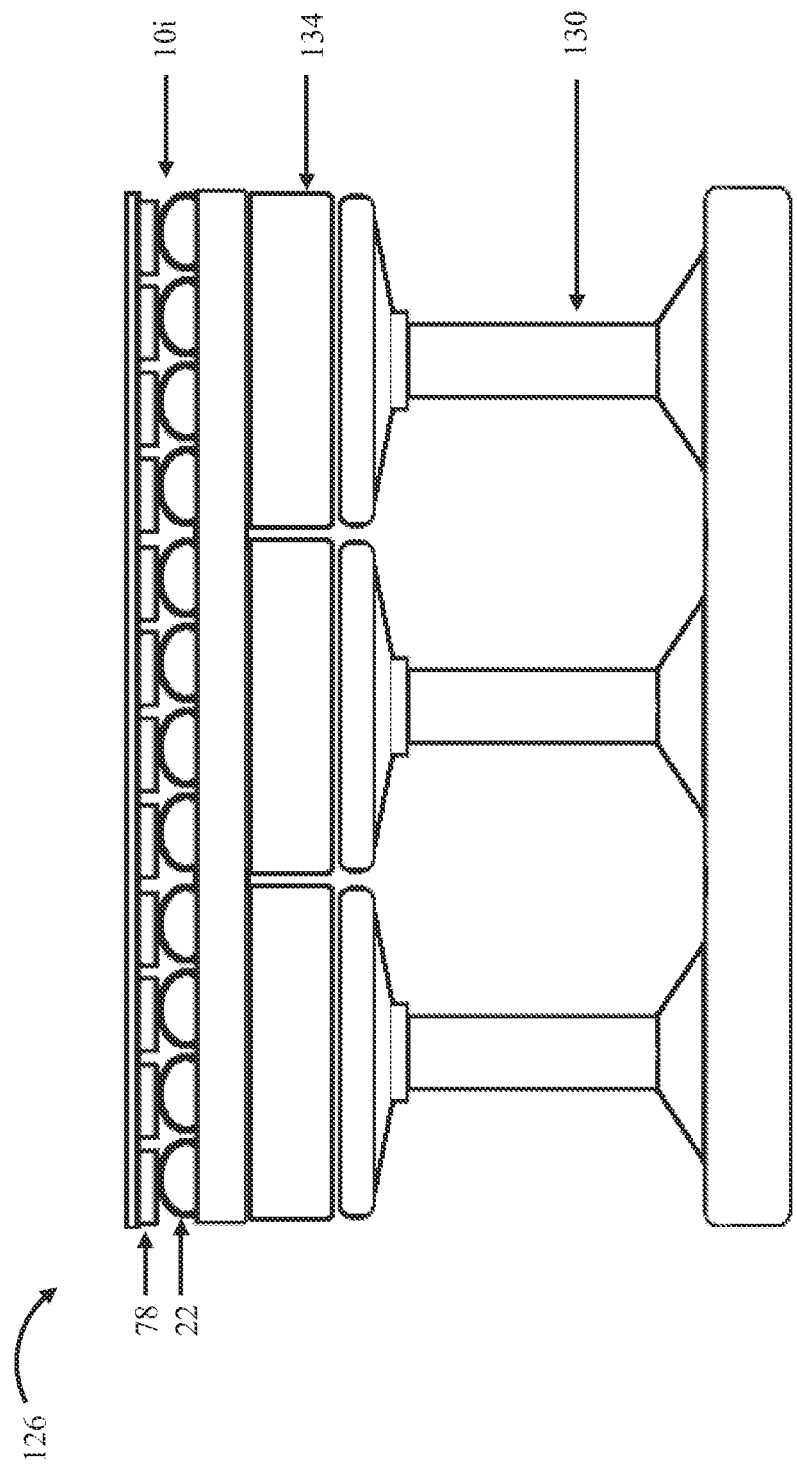
FIG. 8 is a cutaway side view of a bed or seat cushion that comprises a tenth embodiment of the present bubble actuator arrays.

FIG. 8 is a cutaway side view of a bed or seat 126 that comprises a tenth embodiment 10i of the present bubble actuator arrays. In this embodiment, array 10i is depicted as coupled to bed or seat 126; however, array 10i or a similar array may be coupled to any suitable supportive structure, such as, for example, a pillow, and/or the like. Array 10i is substantially similar to array 10d with the primary exception that array 10i is coupled and contoured to an outer surface of bed or seat cushion 126 (e.g., by setting array 10i on a bed or seat cushion and/or securing array 10i relative to the bed or seat cushion, such as, for example, with hook-and-loop fasteners and/or one or more straps) such that array 10i can be actuated to adjust the interface between the bed or seat cushion 126 and a user (e.g., to precisely control the pressure exerted on each portion of a user's body contacted by bed or seat cushion 126). In these and similar embodiments, a cover may be coupled to the array (e.g., comprising a clothing-like material, such as, for example, nylon, cotton, polyester, and/or the like) (e.g., to enhance user comfort).

In these embodiments, bed or seat cushion 126 can further comprise linear displacement tile structures 130 disposed beneath cushion padding 134 to provide for large changes to the pressure exerted on a user by the bed or seat cushion and/or the stiffness and/or the contour of the surface of bed or seat cushion 126. In these embodiments, the bubble actuator arrays (e.g., 10i) may thus be used for fine control over pressure patterns and/or conditions between a user and the bed or seat cushion. As described above for array 10d, array 10i can be configured with sensors (e.g., 78) and a processor (e.g., 54) to be capable of operating in a closed-loop process to ensure desired contact between bed or seat cushion 126 and a user. For example, the sensors can be configured to monitor the pressure exerted on different contacted parts of the user's body by bed or seat cushion 126. A targeted surface pressure value can be maintained by a processor (e.g., 54) by varying the internal pressures (e.g., 42) in cells 22, and thus the deflections (e.g., 50), of a plurality of cells (e.g., 22) through control of a fluid source (e.g., 38) coupled to the plurality of cells (e.g., through fluid passageways 30). This embodiment is thus configured and can be used to ensure safe magnitudes, durations, and/or conditions of contact between a user's body and the bed or seat cushion (e.g., to protect against pressure ulcer formation), and thereby control the pressure exerted by bed or seat cushion on a user.

In these and similar embodiments, cell (e.g., 22) size, shape, and/or the like may be tailored to a specific application. By way of illustration, arrays (e.g., 10i) configured for use in automobile, aircraft, and/or the like seats may comprise cells 22 having transverse dimensions 66 ranging from 25 mm to 153 mm, with heights 68 ranging from 38 mm to 127 mm, arrays configured for use in seat cushions (e.g., office and/or home furniture cushions, and/or the like) may comprise cells 22 having transverse dimensions 66 ranging from 25 mm to 153 mm, with heights 68 ranging from 38 mm to 127 mm, arrays configured for use in mattresses, mattress pads, and/or the like may comprise cells 22 having transverse dimensions 66 ranging from 50 mm to 254 mm, with heights 68 ranging from 25 mm to 305 mm, arrays configured for use in pillows and/or the like may comprise cells 22 having transverse dimensions 66 ranging from 25 mm to 153 mm, with heights 68 ranging from 50 mm to 204 mm, and/or the like. In some embodiments, the present arrays may be configured such that air can flow past an exterior of cells 22 (e.g., to provide for humidity and temperature control).

Figure 9:
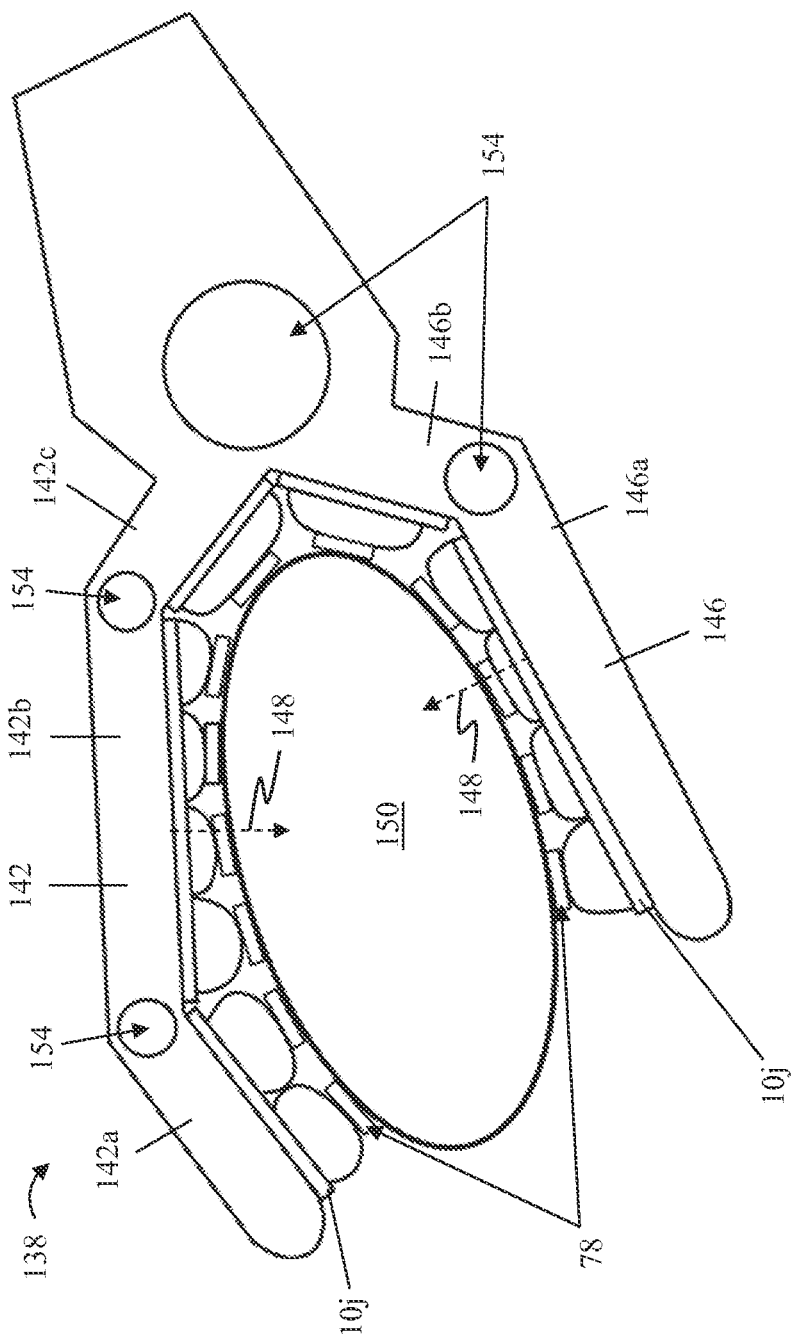
FIG. 9 is a side view of a manipulator that comprises an eleventh embodiment of the present bubble actuator arrays.

FIG. 9 is a side view of a manipulator that comprises a tenth embodiment of the present bubble actuator arrays. In the embodiment shown, manipulator 138 comprises at least two opposing grasping members 142 and 146 (e.g., grasping members 142 and 146 are disposed on substantially opposite sides of manipulator 138). In the embodiment shown, the grasping members are configured to move relative to one another to grasp an object (e.g., 150) (e.g., the relative movement of grasping members is generally indicated by arrows 148). Such movement can be accomplished with one or more actuators (not expressly shown), for example, linear actuator(s), screw-type actuator(s), pneumatic actuator(s), hydraulic actuator(s), and/or the like, and may be controlled and/or monitored by a processor (e.g., which may be the same as or in addition to the processor that can control actuation of array 10*j*, described in more detail below). In the embodiment shown, both grasping members 142 and 146 are configured to move, however, in other embodiments, only one grasping member may be configured to move in order to achieve relative movement between the grasping members. In the embodiment shown, grasping members 142 and 146 comprise segments (e.g., 142*a*, 142*b*, 142*c*, 146*a*, and 146*b*) that are configured to cooperate to facilitate relative movement of the grasping members (e.g., each segment can pivot about a joint 154 to effectuate relative movement of grasping members 142 and 146 generally indicated by arrows 148). In other embodiments, the grasping members can comprise any number of segments (e.g., may comprise only one segment each).

In other embodiments, the relative motion between the grasping members can be accomplished through any different and/or additional structure that permits the functionality described in this disclosure. For example, and not by way of limitation, the grasping members and/or segments may move relative to one another in a translational degree of freedom (e.g., similar to a traditional screw-type clamp) instead of or in addition to a rotational degree of freedom (e.g., through pivoting about joints 154, as described above). In yet other embodiments, the grasping members may not be configured to move relative to one another, and grasping operation of the manipulator can be accomplished solely through actuation of bubble actuator array(s) 10*j*, which are described in more detail below.

In the embodiment shown, manipulator 138 comprises an eleventh embodiment 10*j* of the present bubble actuator arrays or apparatuses. In the embodiment shown, array 10*j* is substantially similar to array 10*d*, with the primary exception that array 10*j* is disposed on and contoured to an outer surface of a grasping member (e.g., 142 and/or 146) of manipulator 138 (e.g., array 10*j* is overlaid onto grasping member(s) of manipulator 138 and can function as an "active skin" of the grasping members). In the embodiment shown, an actuator array 10*j* is disposed on each segment (e.g., 142*a*, 142*b*, 142*c*, 146*a*, and 146*b*) of each grasping member (e.g., as shown, manipulator 138 comprises at least a first array 10*j* disposed on grasping member 142 and a second array 10*j*, different from the first array, disposed on grasping member 146). However, in other embodiments, any number of arrays can be disposed on any number of grasping members that permits the functionality described in this disclosure (e.g., 1, 2, 3, 4, 5, or more arrays disposed on 1, 2, 3, 4, 5, or more grasping members). For example, in some embodiments, the present manipulators can comprise a single array 10*j* that can be disposed on and/or across multiple grasping members (e.g., disposed on grasping members 142 and 146 such that the array is contoured around the opening defined by and between the grasping members).

In embodiments of the present manipulators comprising more than one array (e.g., 138), the arrays can be configured such that the internal pressures of the plurality of cells of at least one array can be varied independently of the internal pressures of the plurality of cells of other arrays (e.g., through configuration of fluid passageways 30, programming of processor 54, and/or connection to separate fluid sources 38). In the embodiment shown, arrays 10*j* are disposed on grasping members 142 and 146 such that at least one array will contact an object (e.g., 150) grasped between the grasping members (e.g., as shown). Through such contact, array(s) 10*j* can be actuated to adjust the interface between grasping members 142 and 146 and a grasped object (e.g., 150). As described above for array 10*d*, array 10*j* can be configured with sensors (e.g., 78) and a processor (e.g., 54) to be capable of operating in a closed-loop process to ensure desired contact (e.g., conformal contact) between grasping members and a grasped object (e.g., 150). For example, the sensors can be configured to monitor the pressure exerted on contacted portions of the grasped object.

In some embodiments, a targeted surface pressure value (e.g., from each sensor) can be maintained by a processor (e.g., 54) by varying the internal pressures (e.g., 42) in cells 22, and thus the pressure exerted by each cell, through control of a fluid source (e.g., 38) coupled to the plurality of cells (e.g., through fluid passageways 30). Through such actuation, pressure between the grasped object and the grasping members can be distributed to prevent over pressuring portions of the grasped object which may cause damage to the object. Such embodiments are thus configured to, and can be used to, precisely control the pressure exerted on a grasped object and/or ensure conformal contact between the grasped object and the grasping members. If conditions between the grasped object and the grasping members change (e.g., the object slips, deforms, and/or is otherwise displaced), the cells of the arrays can be dynamically pressurized and/or depressurized to maintain and/or regain conformal contact with the grasped object. In embodiments with grasping members that are configured to move relative to one another (e.g., 138), the grasping members can be actuated to provide coarse adjustment of the interface between the grasped object and the grasping members (e.g., grasping members can be moved relative to one another until an array 10*j* detects, via sensors 78, a certain pressure and/or contact between the grasped object and the grasping members, for example, during grasping), and/or array 10*j* can be actuated to provide fine control over pressure patterns and/or conditions between the grasping members and the grasped object. Through actuation of arrays 10*j* of manipulator 138, precise control over the grasped object can be exercised without adding additional degrees of freedom to the manipulator (e.g., additional segments, joints, and/or the like). Such fine adjustment provided by array(s) 10j can also reduce the level of precision required in object locating (e.g., the manipulator can be generally positioned near an object to be grasped and the array(s) can be actuated to accomplish grasping operation).

Embodiments of the present manipulators can be used in wide range of applications, and may be particularly suited for applications that require safety and controlled pressure loading (e.g., for grasping sensitive objects). For example, the present manipulators can be used in robotic gripper arms for applications including, but not limited to, manufacturing, surgery, space operations, fruit and/or vegetable picking and/or handling, human robot interactions, and/or the like. The present manipulators can also be configured for use with prosthetic limbs, for example, to allow a user to handle objects of various size, shape, and/or fragility. Prosthetic limbs (e.g., prosthetic arms) which comprise an embodiment of the present manipulators (e.g., 138) may further comprise a socket with one of the present bubble actuator arrays disposed therein to control the conditions between a residual limb and the prosthetic socket (e.g., socket 100, described above).

Some embodiments of the present methods comprise placing an amount of polymer material into a mold configured to form a flexible first layer comprising a plurality of recesses, each recess having a boundary that surrounds a majority of the recess (e.g., layer 14c) and a mold configured to form a flexible second layer that is substantially flat (e.g., layer 20), curing the polymer material, extracting a first layer and a second layer from the molds; and bonding the first layer to the second layer. The extracted top and bottom layers can be bonded together by any means which permit the functionality described in this disclosure, including, but not limited to, through oxygen plasma activation, adhesive, fasteners, melting, and/or use of coupling members disposed on the layers (as described above with reference to FIG. 1A).

Figure 10:
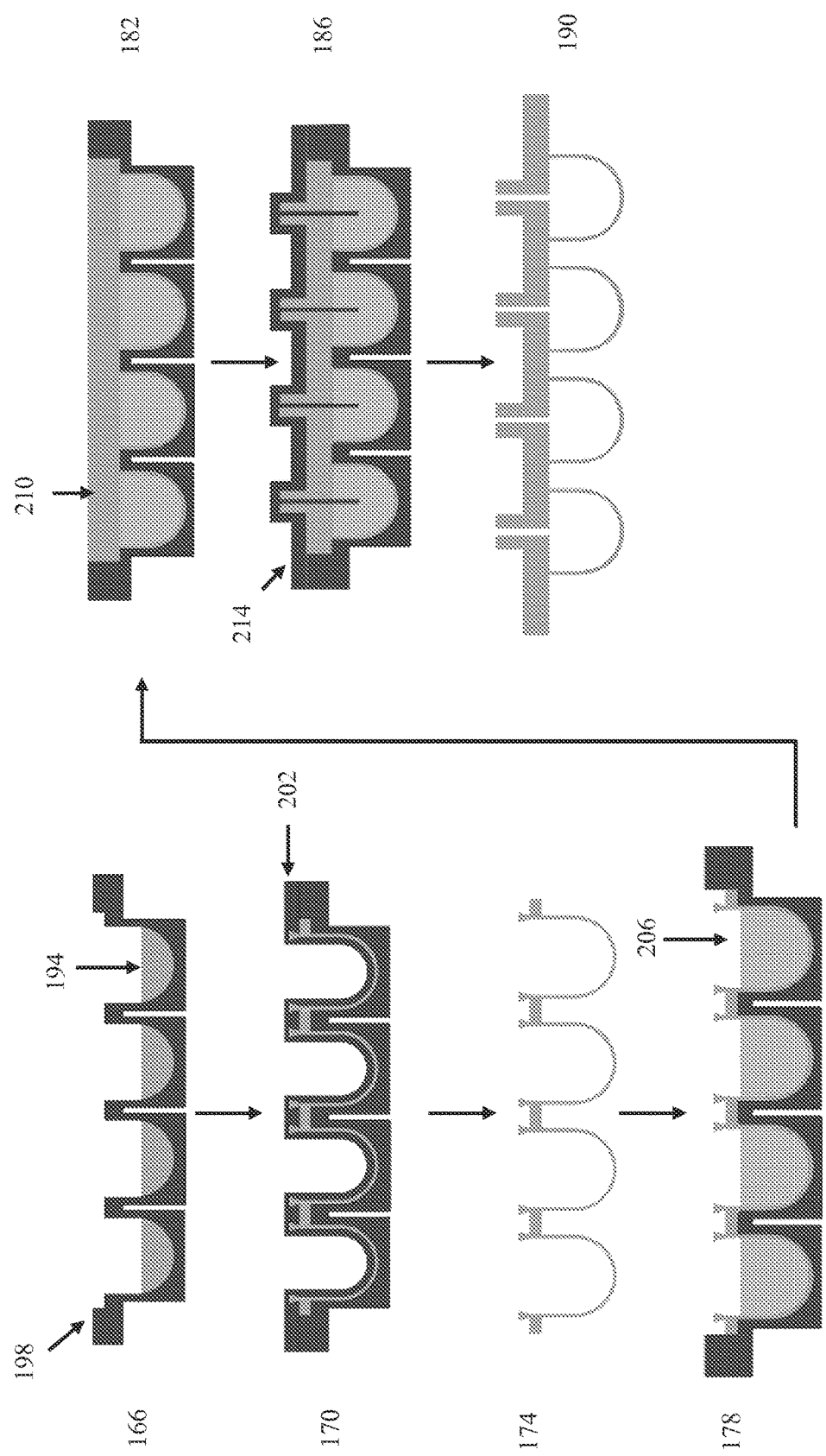
FIG. 10 is a flow chart of one embodiment of the present methods for making an embodiment of the present bubble actuator arrays.

FIG. 10 shows a flow chart of one embodiment of the present methods. In the embodiment shown, the method comprises placing a first amount of polymer material 194 into a first mold piece 198 (166), coupling a second mold piece 202 to the first mold piece to form a flexible first layer having a substantially flat portion and a plurality of second portions each protruding away from the first portion to define a chamber a majority of which is surrounded by a boundary lying on the first portion (e.g., layer 14) (170), and curing the first amount of polymer material (cured first layer (e.g., 14) shown at 174). In this way, the first layer of the bubble actuator arrays (e.g., layer 14) can be molded first. At step 178, the embodiment shown comprises removing the second mold piece 202 and placing a sacrificial material 206 in the chambers of the first flexible layer (178), placing a second amount of polymer material 210 in the first mold piece (182), coupling a third mold piece 214 to the first mold piece to form a substantially flat second layer adjacent to the first layer (e.g., an over-molding process) and comprising a plurality of fluid passageways (e.g., layer 20) (186), extracting the first layer and the second layer from the first piece and removing the sacrificial material from the chambers through the fluid passageways (190) (e.g., to create a sealed first layer 14 and second layer 18 as shown in FIG. 1A). In some embodiments of the present methods, the sacrificial material may be removed from the chambers through the fluid passageways by melting, washing, squeezing, and/or the like. In some embodiments, the sacrificial material comprises gelatin, wax, and/or sugar. However, in other embodiments, any sacrificial material can be used which permits the functionality described in this disclosure (e.g., any material that will prevent the chambers of the first layer from filling with the second amount of polymer material at step 210, and that can later be removed at step 190). In some embodiments of the present methods, a sacrificial material may not be required (e.g., and the function of such a sacrificial material may be performed by third mold piece 214).

In these embodiments, the array layers can be fabricated through compression molding (e.g., pressing the mold pieces together with the polymer material disposed within the mold pieces) and/or injection molding (e.g., placing the mold pieces together before injecting the layer material into the mold). In some embodiments of the present methods, the molds can be fabricated with a three-dimensional (3D) printer, for example, the Viper SLA 3D printer. In these embodiments, the molds can comprise a resin, for example, Accura 25 resin. In other embodiments, the molds may be created through conventional machining and molding processes, for example, constructed out of any suitable material (e.g., aluminum) on a computer numerical control (CNC) or manually operated mill. In some embodiments of the present methods, the mold(s) are coated with an (e.g., sprayable) anti-stiction agent before receiving the polymer material. In further embodiments, the anti-stiction agent is parlyene, and in yet further embodiments, the coating is 1-10 micrometers ($\mu$m) thick (e.g., 3 $\mu$m thick).

Furthermore, in some embodiments of the present methods, the polymer material comprises RTV-4234-T4, provided by Dow Corning under the name XIAMETER, comprising a two component (base and curing agent) thermally curable silicone. In other embodiments, the polymer material can comprise liquid silicone rubber, polyurethane rubber, urethane rubber, natural rubber, polyurethane, nylon, and/or the like. In yet other embodiments, the molds may be formed of a material that allows UV light to reach the polymer material within the mold (e.g., constructed of translucent materials, such as acrylic), and the polymer material may comprise a photosensitive polymer (e.g., such that the polymer material may be cured, at least in part, through exposure to UV light).

Other methods of the present disclosure comprise adjusting with a processor (e.g., 54) and fluid source (e.g., 38) an internal pressure (e.g., 42) of one or more of the plurality of cells (e.g., 22) in a bubble actuator array (e.g., arrays 10, 10a, 10b, 10c, 10d, 10e, 10f, 10g, 10h, 10i, 10j). In further embodiments, the bubble actuator array is in contact with a user (e.g., the user as object 74 in FIG. 4).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

These references, to the extent that they provide exemplary procedural or other details supplementary to those set forth herein, are specifically incorporated herein by reference.

[1] Board W J, Caspers C, Street G M. A comparison of trans-tibial amputee suction and vacuum socket conditions. *Prosthetics and Orthotics International.* 2001; 25: 202-209.

[2] Joan E. Sanders J E, Harrison D S, Allyn K J, and Myers T R, Clinical Utility of In-Socket Residual Limb Volume Change Measurement: Case Study Results *Prosthetics and Orthotics International* 2009; 33: 378-390.

[3] Convery P, and Buis A W. Conventional patellar-tendon-bearing (PTB) socket/stump interface dynamic pressure distributions recorded during the prosthetic stance phase of gait of a trans-tibial amputee, *Prosthetics and Orthotics International* 1998; 22(3):193-8.

[4] Hagberg K. and Branemark R., *Consequences of non-vascular trans femoral amputation: a survey of quality of life, prosthetic use and problems. Prosthetics and Orthotics International* 2001 December; 25(3):186-94.

The invention claimed is:

1. An apparatus comprising:
a flexible first layer comprising a substantially flat first portion and a plurality of second portions each protruding away from the first portion to define a chamber, a majority of which is surrounded by a boundary lying on the first portion;
a flexible second layer that is substantially flat;
where the first layer comprises a plurality of coupling members protruding from the first portion opposite the second portions, the plurality of coupling members embedded in the second layer;
where the first layer is sealed in fixed relation to the second layer along the boundaries to define a plurality of cells between the first layer and the second layer in the chambers and such that the first layer has a surface overlying the cells; and
where the apparatus is configured to be coupled to a fluid source such that the fluid source can deliver fluid to vary internal pressures of the plurality of cells.

2. The apparatus of claim 1, where at least a portion of the surface is smooth such that cells underlying the smooth portion of the surface are configured to deflect the smooth portion of the surface outwardly in at least a lateral and an axial direction under an increased internal pressure of the cells underlying the smooth portion of the surface.

3. The apparatus of claim 1, where at least a portion of the surface is corrugated such that cells underlying the corrugated portion of the surface are configured to deflect the corrugated portion of the surface outwardly in a substantially axial direction under an increased internal pressure of the cells underlying the corrugated portion of the surface.

4. The apparatus of claim 1, where the apparatus is configured such that an internal pressure in at least one of the plurality of cells can be varied independently of an internal pressure in another one of the plurality of cells.

5. The apparatus of claim 1, where at least one of the plurality of cells has a transverse dimension that is different than a corresponding transverse dimension of another one of the plurality of cells.

6. The apparatus of claim 5, where at least some of the plurality of cells sequentially decrease in size along at least one transverse direction of the flexible layers.

7. The apparatus of claim 1, further comprising a plurality of sensors coupled to the apparatus and configured to detect one or more physical characteristics.

8. The apparatus of claim 7, where at least some of the sensors are configured to detect at least one parameter selected from the group consisting of: pressure, shear force, temperature, and pH.

9. The apparatus of claim 7, further comprising a processor configured to control the fluid source to adjust the internal pressure in the plurality of cells at least partly based on data detected by the sensors.

10. The apparatus of claim 1, further comprising:
a memory configured to store pressure patterns; and
a processor in communication with the memory and configured to control the fluid source to adjust the internal pressure in the plurality of cells at least partly based on the pressure patterns.

11. The apparatus of claim 1, where the apparatus is configured to be coupled to a bed or a seat.

12. An apparatus comprising:
a flexible first layer comprising a first side that is substantially flat and a second side having a substantially flat first portion and a plurality of second portions each protruding inward toward the first side to define a recess, a majority of which is surrounded by a boundary lying on the first portion;
a flexible second layer;
where the first layer comprises a plurality of coupling members protruding from the first portion opposite the second portions, the plurality of coupling members embedded in the second layer;
where the first layer is sealed in fixed relation to the second layer along the boundaries to define a plurality of cells between the first layer and the second layer in the recesses and such that a surface of either the first layer or the second layer overlies the cells; and
where the apparatus is configured to be coupled to a fluid source such that the fluid source can deliver fluid to vary internal pressures of the plurality of cells.

13. The apparatus of claim 12, where a surface of the first layer overlies at least some of the plurality of cells and a surface of the second layer overlies at least some of the plurality of cells.

14. An apparatus comprising:
a flexible first layer comprising a substantially flat first portion and a plurality of second portions each protruding away from the first portion to define a chamber, a majority of which is surrounded by a boundary lying on the first portion;
a flexible second layer that is substantially flat;
where the first layer is sealed in fixed relation to the second layer along the boundaries to define a plurality of cells between the first layer and the second layer in the chambers and such that the first layer has a surface overlying the cells;
where the apparatus is configured to be coupled to a fluid source such that the fluid source can deliver fluid to vary internal pressures of the plurality of cells; and where the apparatus is configured such that a maximum displacement of the surface overlying at least one of cells is between 2% and 15% of a transverse dimension of the cell for each pound per square inch (psi) increase in internal pressure between 1 psi and 5 psi.

15. An apparatus comprising:
a flexible first layer comprising a substantially flat first portion and a plurality of second portions each protruding away from the first portion to define a chamber, a majority of which is surrounded by a boundary lying on the first portion;
a flexible second layer that is substantially flat;
where the first layer is sealed in fixed relation to the second layer along the boundaries to define a plurality of cells between the first layer and the second layer in the chambers and such that the first layer has a surface overlying the cells; and
a fluid source configured to be coupled to the layers and to deliver fluid to vary internal pressures in the plurality of cells.

16. An apparatus comprising:
a flexible first layer comprising a substantially flat first portion and a plurality of second portions each protruding away from the first portion to define a chamber, a majority of which is surrounded by a boundary lying on the first portion;
a flexible second layer that is substantially flat;
where the first layer is sealed in fixed relation to the second layer along the boundaries to define a plurality of cells between the first layer and the second layer in the chambers and such that the first layer has a surface overlying the cells;
where the apparatus is configured to be coupled to a fluid source such that the fluid source can deliver fluid to vary internal pressures of the plurality of cells; and
where the apparatus is configured to be coupled to at least one item selected from the group consisting of: a prosthesis socket, a helmet, seat cushion, bed, mattress, pillow, and a prosthetic limb.

17. A manipulator comprising:
at least two opposing grasping members configured to move relative to one another to grasp an object; and
an apparatus disposed on at least one of the grasping members such that the apparatus will contact an object grasped between the grasping members, the apparatus comprising:
a flexible first layer comprising a substantially flat first portion and a plurality of second portions each protruding away from the first portion to define a chamber, a majority of which is surrounded by a boundary lying on the first portion;
a flexible second layer that is substantially flat;
where the first layer is sealed in fixed relation to the second layer along the boundaries to define a plurality of cells between the first layer and the second layer in the chambers and such that the first layer has a surface overlying the cells; and
where the apparatus is configured to be coupled to a fluid source such that the fluid source can deliver fluid to vary internal pressures of the plurality of cells.

18. The manipulator of claim 17, further comprising a second apparatus, the second apparatus comprising:
a flexible first layer comprising a substantially flat first portion and a plurality of second portions each protruding away from the first portion to define a chamber, a majority of which is surrounded by a boundary lying on the first portion;
a flexible second layer that is substantially flat;
where the first layer is sealed in fixed relation to the second layer along the boundaries to define a plurality of cells between the first layer and the second layer in the chambers and such that the first layer has a surface overlying the cells; and
where the second apparatus is configured to be coupled to a fluid source such that the fluid source can deliver fluid to vary internal pressures of the plurality of cells.

19. A system comprising:
robotic gripper or prosthetic, where the robot gripper or prosthetic comprises a manipulator, the manipulator comprising:
at least two opposing grasping members configured to move relative to one another to grasp an object; and
an apparatus disposed on at least one of the grasping members such that the apparatus will contact an object grasped between the grasping members, the apparatus comprising:
a flexible first layer comprising a substantially flat first portion and a plurality of second portions each protruding away from the first portion to define a chamber, a majority of which is surrounded by a boundary lying on the first portion;
a flexible second layer that is substantially flat;
where the first layer is sealed in fixed relation to the second layer along the boundaries to define a plurality of cells between the first layer and the second layer in the chambers and such that the first layer has a surface overlying the cells; and
where the apparatus is configured to be coupled to a fluid source such that the fluid source can deliver fluid to vary internal pressures of the plurality of cells.

* * * * *